(12) United States Patent
Bielsa Guivernau et al.

(10) Patent No.: US 10,543,249 B2
(45) Date of Patent: Jan. 28, 2020

(54) PHARMACEUTICAL COMPOSITION FOR A SUSTAINED RELEASE OF LANREOTIDE

(71) Applicant: IPSEN PHARMA S.A.S., Boulogne-Billancourt (FR)

(72) Inventors: Ruth Bielsa Guivernau, Palleja (ES); Roland Cherif-Cheikh, Castelldefels (ES); Julie Fournes, Sant Pere de Ribes (ES); Daniel Martinez Lorente, Sabadell (ES); Anne Petit, Leves (FR); Joël Richard, Méré (FR)

(73) Assignee: IPSEN PHARMA S.A.S., Boulogne-Billancourt (FR)

( * ) Notice: Subject to any disclaimer, the term of this patent is extended or adjusted under 35 U.S.C. 154(b) by 0 days.

(21) Appl. No.: 14/903,010

(22) PCT Filed: Jul. 8, 2014

(86) PCT No.: PCT/EP2014/064586
§ 371 (c)(1),
(2) Date: Jan. 5, 2016

(87) PCT Pub. No.: WO2015/004125
PCT Pub. Date: Jan. 15, 2015

(65) Prior Publication Data
US 2016/0151447 A1 Jun. 2, 2016

(30) Foreign Application Priority Data
Jul. 9, 2013 (EP) ..................................... 13290156

(51) Int. Cl.
*A61K 38/08* (2019.01)
*A61K 9/00* (2006.01)
*A61K 47/12* (2006.01)

(52) U.S. Cl.
CPC ............ *A61K 38/08* (2013.01); *A61K 9/0019* (2013.01); *A61K 47/12* (2013.01)

(58) Field of Classification Search
None
See application file for complete search history.

(56) References Cited

U.S. PATENT DOCUMENTS

| | | |
|---|---|---|
| 6,503,534 B1 | 1/2003 | Pellet et al. |
| 9,352,012 B2 | 5/2016 | Montes et al. |
| 2003/0044463 A1 | 3/2003 | Deghenghi et al. |
| 2004/0247672 A1 | 12/2004 | Tracy et al. |
| 2007/0116729 A1 | 5/2007 | Palepu et al. |
| 2009/0092650 A1* | 4/2009 | Warren ................ A61K 9/0021 424/422 |
| 2011/0178013 A1 | 7/2011 | Paternostre et al. |
| 2011/0183905 A1 | 7/2011 | Schönhammer |
| 2011/0250243 A1* | 10/2011 | Kissel ...................... A61K 9/10 424/400 |
| 2012/0172650 A1* | 7/2012 | Katznelson ............ A61K 38/31 600/1 |
| 2012/0183629 A1* | 7/2012 | Dunn ................... A61K 9/0024 424/649 |

FOREIGN PATENT DOCUMENTS

| | | |
|---|---|---|
| CN | 1415378 A | 5/2003 |
| EP | 1595532 | 11/2005 |
| FR | 2762319 | 10/1998 |
| WO | 96/07398 | 3/1996 |
| WO | 01/89479 | 11/2001 |
| WO | 2006/066868 | 6/2006 |
| WO | 2008/152401 | 12/2008 |
| WO | 2009040035 | 4/2009 |
| WO | 2011/085957 | 7/2011 |
| WO | WO 20110859957 * | 7/2011 |

OTHER PUBLICATIONS

Jorgensen et al. Intranasal absorption of different aqueous formulations. International Journal of Pharmaceutics.113 (1995) 83-87. https://pdf.sciencedirectassets.com/271189/1-s2.0-S0378517300X00476/1-s2.0-0378517394001825/main.pdf?x-amz-security-token=AgoJb3JpZ2luX2VjEDcaCXVzLWVhc3QtMSJHM EUCIG8uWDRSEGphxKFJHfNzitv.*
International Search Report and Written Opinion for PCT/EP14/064586 dated Jan. 15, 2015.
Somatuline Depot (lanreotide acetate); Approved, Aug. 2007.
International Search Report for PCT/EP2011/000069, dated Mar. 12, 2012.

* cited by examiner

*Primary Examiner* — Maury A Audet
(74) *Attorney, Agent, or Firm* — Gene J. Yao; Barnes & Thornburg LLP

(57) ABSTRACT

A pharmaceutical composition for a sustained release of peptide therapeutics, in particular for a sustained release compatible with therapeutic treatments of at least two months. In an embodiment, the composition comprises lanreotide as an active agent, a hydrosoluble co-solvent, and water with the pH of the composition being from 4.0 to 7.5.

7 Claims, 6 Drawing Sheets

PHARMACEUTICAL COMPOSITION FOR A SUSTAINED RELEASE OF LANREOTIDE

CROSS-REFERENCE TO RELATED APPLICATIONS

This application is the U.S. National Phase of International Patent Application No. PCT/EP2014/064586, filed Jul. 8, 2014, which claims the benefit of European Patent Application No. 13290156.2, filed Jul. 9, 2013, the contents of each of which are hereby incorporated by reference in their entireties.

FIELD OF THE INVENTION

The present invention relates to a pharmaceutical composition for a sustained release of peptide therapeutics, in particular for a sustained release compatible with therapeutic treatments of at least 2 months. In some preferred embodiments, the pharmaceutical composition comprises the peptide lanreotide. Such pharmaceutical compositions are particularly useful for the treatment of diseases lanreotide is indicated for.

BACKGROUND OF THE INVENTION

Lanreotide is a marketed somatostatin analogue. It is a cyclic peptide with the amino acid sequence presented below:

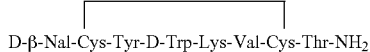

D-β-Nal-Cys-Tyr-D-Trp-Lys-Val-Cys-Thr-NH$_2$ wherein Nal is the abbreviation for naphthylalanine, and there is a disulfide bridge between the two cysteine residues.

Lanreotide is indicated in the treatment of acromegaly due to both pituitary and non-pituitary growth hormone-secreting tumors, the management of symptoms caused by neuroendocrine tumors (NET), particularly carcinoid tumors and VIPomas (VIP=Vasoactive Intestinal Peptide), and in the treatment of thyrotrophic adenoma.

The treatments require continuous or repeated administration to the patient over an extended period of time. As repeated injections cause both inconvenience and discomfort to the patient, sustained release preparations are desirable and have been the subject of development efforts. Thus lanreotide is available today in two formulations: a sustained release formulation which is injected intramuscularly every ten or fourteen days and an extended release formulation which is administered subcutaneously once a month or once every 2 months for certain acromegalic patients. However, even if this set of extended release formulations exists, a need remains to reduce both inconvenience and discomfort to the patient with extended release formulations covering more than 2 months or even 2 months for the patients not covered by the existing formulations.

To extend the duration of treatment for more than one month, in particular for at least two months, the amount of injected pharmaceutical active ingredient (injected dose) has to be increased. On the other hand, to avoid further discomfort for the patient, the injected volume must remain as low as possible and compatible with the parenteral administration route. Therefore, there is need for a new pharmaceutical composition of lanreotide capable of delivering a sustained release over at least two months, preferably with a high dose of lanreotide (e.g. 120, 240 or 360 mg) while keeping a convenient volume of injection (e.g. equal or less than 2 mL). The present invention provides such pharmaceutical compositions.

SUMMARY OF THE INVENTION

The subject of the present invention is thus a pharmaceutical composition for a sustained release of the active ingredient for at least 2 months, comprising:
  lanreotide as the active ingredient,
  a hydrosoluble co-solvent, and
  water,
the pH of the composition ranging from 4.0 to 7.5.

DETAILED DESCRIPTION OF THE INVENTION

Figure 1:
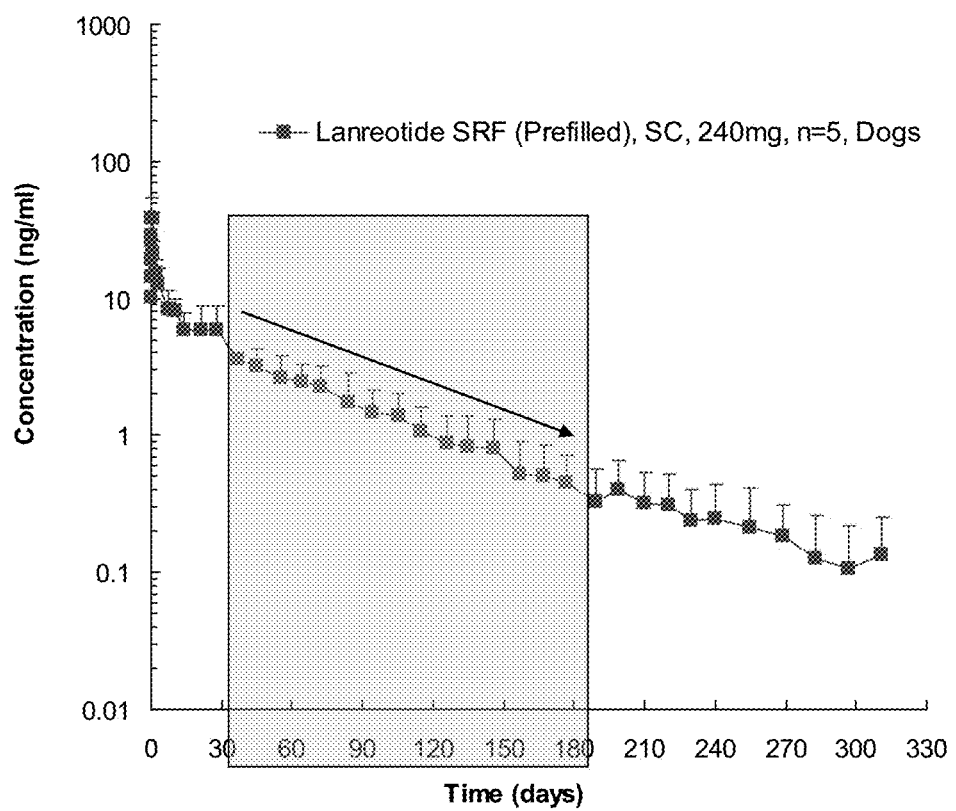
FIG. 1 depicts the pharmacokinetic profile obtained following the administration of a 240 mg dose of lanreotide, using a composition comprising lanreotide, glycofurol, acetic acid, and water.

In the text herein below, unless otherwise indicated, the limits of a range of values are included in that range, especially in the expression "ranging from".

Unless otherwise indicated the following definitions are set forth to illustrate and define the meaning and scope of the various terms used to describe the invention herein.

The term "pH modifier" as used herein refers to a compound or excipient used mainly to adjust or control the pH of the formulation.

The term "co-solvent" as used in the present application refers to a solvent or a mixture of solvents which allows the incorporation of the active ingredient in the composition to obtain the required dose in a suitable volume and matching the injectability criteria. In the co-solvent, the solubility of lanreotide or its salts used according to the present invention is preferably equal or higher than 8% (w/v) at room temperature (20-25° C.).

The term "hydrosoluble" is understood to mean soluble in water. Preferably, the "hydrosoluble" co-solvent has solubility in water measured at 25° C. higher than 10 mg/mL, and preferably higher than 30 mg/mL.

The term "non hydrosoluble" is understood to mean non soluble in water. Preferably, a "non hydrosoluble" (co) polymer or excipient has solubility in water measured at 25° C. less than 1 mg/mL, and preferably less than 0.1 mg/mL.

The term "low molecular weight" is understood to mean that the molecular weight is less than 2,000 Da.

The term "aprotic" when used to describe a solvent is understood to mean a solvent unable to freely release a proton H+ in solution, and unable to modify the pH when added to a composition in the pH range of 4 to 8.

The term "injectability" which can be determined by measuring the injection force, refers to the suitability of the formulation for parenteral administration using a device for injection, like a syringe or an injector.

The term "stabilizer" as used herein means a pharmaceutically acceptable compound to prevent degradation, enhance the physical or chemical stability of the active substance (e.g. a compound having antioxidant properties or surfactants).

The term "surfactant" as used herein refers to a compound or excipient with surface active properties. When used in the present formulations, a surfactant may improve the aqueous solubility of the active ingredient, help to protect the active substance against degradation, and/or limit active ingredient precipitation if co-solvent alone is not sufficient.

The term "antioxidant" as used herein refers to a compound having antioxidant properties. When used in the present formulations, the antioxidant may inhibit or prevent oxidative degradation of the active ingredient and/or inhibit or prevent oxidative degradation of the excipients.

The term "(co)polymer" means a polymer or copolymer or a mixture thereof.

The term "biocompatible" means biologically compatible by not producing a medically significant toxic, injurious, or immunological response in living tissues, biological systems or biological functions.

The term "biodegradable" means capable of being decomposed by biological agents, biological (micro-)organisms, or when placed in biological fluids.

The term "essentially" when used associated with the expression "a composition consisting essentially of" means that any additional components constitute only minor impurities, individually less than 2, preferably less than 1, more preferably less than 0.5, 0.25% relative to the total weight of the composition, and in aggregate less than 3, 2, 1, 0.5% relative to the total weight of the composition.

In a preferred embodiment, "a composition consisting essentially of" means that any additional components constitute only minor impurities, individually less than 2% relative to the total weight of the composition, and in aggregate less than 3% relative to the total weight of the composition.

In a preferred embodiment, "a composition consisting essentially of" means that any additional components constitute only minor impurities, individually less than 1% relative to the total weight of the composition, and in aggregate less than 2% relative to the total weight of the composition.

In a preferred embodiment, "a composition consisting essentially of" means that any additional components constitute only minor impurities, individually less than 0.5% relative to the total weight of the composition, and in aggregate less than 1% relative to the total weight of the composition.

In a preferred embodiment, "a composition consisting essentially of" means that any additional components constitute only minor impurities, individually less than 0.25% relative to the total weight of the composition, and in aggregate less than 0.5% relative to the total weight of the composition.

Unless otherwise stated, all percentages mentioned in the present invention are weight/weight (w/w) percentages.

The active ingredient lanreotide is in the form of a salt or as a free-base. The salts of lanreotide which can be used for the invention are preferably pharmaceutically acceptable salts of organic acids, such as those of acetic, phenylacetic, lactic, malic, pamoic, ascorbic, succinic, benzoic, methanesulphonic or toluenesulphonic acids, or pharmaceutically acceptable salts of inorganic acids, such as those of hydrochloric, hydrobromic, hydriodic, sulphuric or phosphoric acids.

According to one preferred embodiment, lanreotide is in a salt form.

Preferably, lanreotide is in the form of lanreotide acetate.

According to another preferred embodiment, lanreotide is as a free base.

Whatever the form of lanreotide, i.e. salt form or free base, in the sense of the present invention, the amount of lanreotide, expressed for instance as a concentration or a percentage in the composition, refers to lanreotide as a free base.

Advantageously, lanreotide is present in a concentration ranging from 35 to 55% by weight, preferably from 40 to 50% by weight, and more preferably from 42 to 48% by weight relative to the total weight of the composition. In another preferred embodiment, lanreotide is present in a concentration ranging from 42 to 46% by weight relative to the total weight of the composition.

A composition according to the present invention comprises a co-solvent which allows obtaining the required injectability criteria of the pharmaceutical compositions. The co-solvent used in the composition according to the present invention is hydrosoluble. Moreover, the solubility, in the hydrosoluble co-solvent, of lanreotide or its salts used according to the present invention is equal or higher than 8% (w/v) at room temperature. For comparison, the solubility of lanreotide acetate is less than 4% in water, aqueous acetic acid (at the concentration of 0.1 or 1 mol/mL), aqueous NaCl (0.9%), or polysorbate (0.01%).

The co-solvent may be selected from low molecular weight hydrosoluble polymers such as polyvinylpyrrolidone (PVP), polyethylene glycol (PEG) or a mixture thereof, and in particular PEG 600, PEG 500-DME (dimethyl ether), PEG 500, PEG 400, PEG 300, PEG 200 or a mixture thereof.

The co-solvent may preferably be an aprotic solvent. The aprotic co-solvent used according to the present invention does not significantly modify, or is unable to modify, the pH value in the pH range of 4 to 8. Such aprotic solvent may be selected from N-methyl-2-pyrrolidone (NMP), N-ethyl-2-pyrrolidone (NEP), glycofurol, propylene glycol, ethanol, benzyl alcohol and mixtures thereof, In a preferred embodiment, the hydrosoluble co-solvent is selected from the low molecular weight hydrosoluble polymers and mixtures thereof.

In a preferred embodiment, the hydrosoluble co-solvent is an aprotic solvent.

In another preferred embodiment, the co-solvent is selected from N-methyl-2-pyrrolidone (NMP), propylene glycol, glycerol, low molecular weight polyethylene glycols (PEG), glycofurol, ethanol and a mixture thereof, and more preferably from NMP, low molecular weight PEG, glycofurol and mixtures thereof.

In a preferred embodiment, the co-solvent is present in a concentration ranging from 10 to 25% by weight, and more preferably from 15 to 22% by weight relative to the total weight of the composition.

In a more preferred embodiment, the co-solvent is NMP. Preferably, the co-solvent is NMP and is present in a concentration ranging from 15 to 20% by weight relative to the total weight of the composition.

In another embodiment, the co-solvent is a low molecular weight PEG. Preferably, the co-solvent is a low molecular weight PEG and is present in a concentration ranging from 15 to 22% by weight relative to the total weight of the composition.

In a more preferred embodiment, the co-solvent is glycofurol. Preferably, the co-solvent is glycofurol and is present in a concentration ranging from 16 to 22% by weight relative to the total weight of the composition. Preferably, the co-solvent is glycofurol and is present in a concentration ranging from 16 to 20% by weight relative to the total weight of the composition.

In another preferred embodiment, the co-solvent is glycofurol of formula (1)

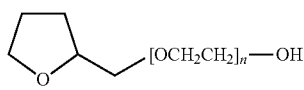

wherein n is an integer from 1 to 5, or a mixture thereof,
According to the present invention, the formula (1) covers the racemic as well as the enantiomeric forms of the compound.

In another preferred embodiment, the co-solvent is glycofurol of formula (1) as defined above or a mixture thereof, and is present in a concentration ranging from 16 to 20% by weight relative to the total weight of the composition.

In another preferred embodiment, the co-solvent is glycofurol of formula (1) as defined above or a mixture thereof, wherein n is an integer from 1 to 2, and is present in a concentration ranging from 16 to 20% by weight relative to the total weight of the composition.

As the composition is intended for parenteral administration, the pH of the composition must be controlled for a local tolerance and tolerability point of view, and this parameter plays also a role on active substance solubilisation and drug product sustained release properties. Thus the pH of the composition is between 4.0 and 7.5.

In a preferred embodiment of the invention, the pH of the composition is from 4.0 to 6.0 and preferably from 4.8 to 5.4.

To reach a pH ranging from 4.0 to 7.5, depending on the lanreotide form and the salt form in particular, a pH modifier may be needed.

In another embodiment, the composition according to the present invention comprises an optional pH modifier.

In a preferred embodiment, the present invention is a pharmaceutical composition for a sustained release of the active ingredient for at least 2 months, said composition comprising or consisting essentially of, or consisting of:
  lanreotide as the active ingredient,
  a hydrosoluble co-solvent,
  an optional pH modifier, and
  water,
the pH of the composition ranging from 4.0 to 7.5.

In a more preferred embodiment, the composition of the present invention comprises an optional pH modifier and the pH is ranging from 4.0 to 6.0.

Another subject of the present invention is a pharmaceutical composition for a sustained release of an active ingredient for at least 2 months, said composition comprising or consisting essentially of, or consisting of:
  lanreotide as the active ingredient,
  a hydrosoluble co-solvent,
  an optional pH modifier, and
  water (for injection),
the pH of the composition ranging from 4.0 to 6.0.

In a preferred embodiment, the present invention is a pharmaceutical composition for a sustained release of the active ingredient for at least 2 months, said composition comprising or consisting essentially of, or consisting of:
  lanreotide as the active ingredient,
  a hydrosoluble aprotic co-solvent,
  an optional pH modifier, and
  water,
the pH of the composition ranging from 4.0 to 7.5, and preferably from 4.0 to 6.0. The pH modifier may be chosen, for instance, from acetic acid, citric acid, lactic acid, phosphoric acid, hydrochloric acid, stearic acid and pamoic acid. If used, the pH modifier may be different from the hydrosoluble co-solvent.

In another embodiment, the composition according to the present invention comprises a pH modifier. In another preferred embodiment, the composition according to the present invention comprises a pH modifier and said pH modifier is different from the co-solvent.

In another embodiment, the pharmaceutical composition of the present invention is for a sustained release of an active ingredient for at least 2 months, and comprising or consisting essentially of, or consisting of:
  lanreotide as the active ingredient,
  a hydrosoluble co-solvent,
  a pH modifier, and
  water (for injection),
the pH of the composition ranging from 4.0 to 6.0.

In a preferred embodiment, the present invention is a pharmaceutical composition for a sustained release of the active ingredient for at least 2 months, said composition comprising or consisting essentially of, or consisting of:
  lanreotide as the active ingredient,
  a hydrosoluble aprotic co-solvent, a pH modifier, and
water,
the pH of the composition ranging from 4.0 to 7.5, and preferably from 4.0 to 6.0.

In another preferred embodiment, the pharmaceutical composition according to the invention is for a sustained release of an active ingredient for at least 2 months and comprises or consists essentially of, or consisting of:
from 35 to 55% of lanreotide as the active ingredient,
from 10 to 25% of a hydrosoluble aprotic co-solvent,
a pH modifier, and
water (qsp 100%),
the pH of the composition ranging from 4.0 to 7.5, and preferably from 4.0 to 6.0.

In another embodiment, the pharmaceutical composition of the present invention is for a sustained release of an active ingredient for at least 2 months and comprises or consists essentially of, or consisting of:
lanreotide as the active ingredient,
a hydrosoluble co-solvent,
a pH modifier, and
water (for injection),
the pH of the composition ranging from 4.0 to 7.5 and the pH modifier being different from the hydrosoluble co-solvent.

Preferably, the pH modifier is added to reach a target pH value ranging from 4.0 to 7.5, preferably from 4.0 to 6.0, and more preferably from 4.8 to 5.4.

In another preferred embodiment, the pharmaceutical composition according to the invention is for a sustained release of an active ingredient for at least 2 months and comprises or consists essentially of, or consisting of:
from 35 to 55% of lanreotide as the active ingredient,
from 10 to 25% of a hydrosoluble co-solvent,
a pH modifier, and
water (qsp 100%),
the pH of the composition ranging from 4.0 to 7.5, more preferably from 4.0 to 6.0, and the pH modifier being different from the hydrosoluble co-solvent. In a preferred embodiment of the invention, the pH modifier is present and selected from acetic acid, citric acid, lactic acid, phosphoric acid, hydrochloric acid, stearic acid and pamoic acid, and preferably is acetic acid.

In another preferred embodiment, the pharmaceutical composition according to the present invention is free of any non hydrosoluble, biocompatible and/or biodegradable, (co)polymer or a mixture thereof. This means that the content of any non hydrosoluble, biocompatible and/or biodegradable, (co)polymer in the composition is less than 0.1% by weight (w/w).

A classical and well-described way to provide a pharmaceutical composition with a sustained release of an active pharmaceutical ingredient after administration is the use of biocompatible (co)polymers such as polylactides (PLA), polyglycolides (PLG), poly lactide-co-glycolides (PLGA), polyalkylcyanoacrylates, poly-ε-caprolactones and any (co)polymer agents obtained by combination or modification of these biocompatible (co)polymers. Such (co)polymers which are not hydrosoluble form the biodegradable matrix of microparticles or solid implants, which is progressively eroded when administered into the body.

In another preferred embodiment, the pharmaceutical composition of the present invention is for a sustained release of the active ingredient for at least 2 months, free of any non hydrosoluble, biocompatible and/or biodegradable, (co)polymer, and comprising or consisting essentially of, or consisting of:
lanreotide as the active ingredient,
a hydrosoluble co-solvent,
an optional pH modifier, and
water,
the pH of the composition ranging from 4.0 to 7.5,
and more preferably comprising or consisting essentially of, or consisting of
from 35 to 55% of lanreotide as the active ingredient,
from 10 to 25% of a hydrosoluble co-solvent,
an optional pH modifier, and
water (qsp 100%),
the pH of the composition ranging from 4.0 to 7.5, and more preferably from 4.0 to 6.0.

In another preferred embodiment, the pharmaceutical composition of the present invention is for a sustained release of an active ingredient for at least 2 months, free of any non hydrosoluble, biocompatible and/biodegradable, (co)polymer, and comprising or consisting essentially of, or consisting of:
lanreotide as the active ingredient,
a hydrosoluble co-solvent,
a pH modifier, and
water,
the pH of the composition ranging from 4.0 to 7.5 and the pH modifier being different from the hydrosoluble co-solvent,
and more preferably comprising or consisting essentially of or consisting
from 35 to 55% of lanreotide as the active ingredient,
from 10 to 25% of a hydrosoluble co-solvent,
a pH modifier, and
water (qsp 100%),
the pH of the composition ranging from 4.0 to 7.5, and more preferably from 4.0 to 6.0, and the pH modifier being different from the hydrosoluble co-solvent.

In another preferred embodiment, the pharmaceutical composition of the present invention is for a sustained release of an active ingredient for at least 2 months, free of any non hydrosoluble, biocompatible and/biodegradable, (co)polymer, and comprising or consisting essentially of or consisting
lanreotide as the active ingredient,
a hydrosoluble aprotic co-solvent,
a pH modifier, and
water,
the pH of the composition ranging from 4.0 to 7.5,
and more preferably comprising or consisting essentially of or consisting of
from 35 to 55% of lanreotide as the active ingredient,
from 10 to 25% of a hydrosoluble aprotic co-solvent,
a pH modifier, and
water (qsp 100%),
the pH of the composition ranging from 4.0 to 7.5, and more preferably from 4.0 to 6.0.

A composition according to the present invention may also contain other additives usually used in such pharmaceutical compositions such as, for instance, stabilizers, antioxidants or surfactants.

Stabilizers or surfactants may be selected from fatty acids and salts thereof, polyoxyethers, poloxamers, polyols such as trehalose, mannitol, saccharose and dextrose, polysorbates, polyoxyethylene fatty acid esters, and mixtures thereof.

Antioxidants may be selected from: amino acids such as methionine, histidine, tryptophan; polyamino acids such as glutathione; chelating agents such as disodium edetate (EDTA) and citric acid; sodium metabisulfite; butylhydroxytoluene (BHT); butylhydroxyanisol; ascorbic acid; and mixtures thereof. Preferably, the antioxidant is selected from amino acids, polyamino acids, and mixtures thereof, and more preferably from methionine, histidine, tryptophan and glutathione.

If present, the amount in weight (w/w) of these additives is lower than 5.0% of the pharmaceutical composition, and preferably lower than 1.0%.

In a preferred embodiment, the composition according to the present invention comprises an additive selected from stabilizers, antioxidants, surfactants, and mixtures thereof, in an amount lower than 5.0% (w/w) of the pharmaceutical composition, and preferably lower than 1.0%.

In a preferred embodiment, the composition according to the present invention comprises an antioxidant, in an amount lower than 5.0% (w/w) of the pharmaceutical composition, and preferably lower than 1.0%.

In another preferred embodiment, the composition according to the present invention comprises an antioxidant selected from amino acids, polyamino acids, and mixtures thereof, in an amount lower than 5.0% (w/w) of the pharmaceutical composition, and preferably lower than 1.0%.

In another preferred embodiment, the composition according to the present invention comprises an antioxidant selected from methionine, histidine, tryptophan and glutathione, and mixtures thereof, in an amount lower than 5.0% (w/w) of the pharmaceutical composition, and preferably lower than 1.0%.

In another preferred embodiment, the composition according to the invention is for a sustained release of an active ingredient for at least 2 months and consists of:
from 35 to 55% of lanreotide as the active ingredient,
from 10 to 25% of a hydrosoluble aprotic co-solvent,
a pH modifier,
from 0 to 5% of an additive selected from stabilizers, antioxidants, surfactants, and mixtures thereof, and
water (qsp 100%),
the pH of the composition ranging from 4.0 to 7.5.

In another preferred embodiment, the composition according to the invention is for a sustained release of an active ingredient for at least 2 months and consists of:
from 35 to 55% of lanreotide as the active ingredient,
from 10 to 25% of a hydrosoluble aprotic co-solvent,
a pH modifier,
from 0 to 1% of an additive selected from stabilizers, antioxidants, surfactants, and mixtures thereof, and
water (qsp 100%),
the pH of the composition ranging from 4.0 to 6.0.

In another preferred embodiment, the composition according to the invention is for a sustained release of an active ingredient for at least 2 months and consists of:
from 35 to 55% of lanreotide as the active ingredient,
from 10 to 25% of a hydrosoluble co-solvent,
a pH modifier,
from 0 to 5% of an additive selected from stabilizers, antioxidants, surfactants, and mixtures thereof, and
water (qsp 100%),
the pH of the composition ranging from 4.0 to 7.5, and the pH modifier being different from the hydrosoluble co-solvent.

In another preferred embodiment, the composition according to the invention is for a sustained release of an active ingredient for at least 2 months and consists of:
from 35 to 55% of lanreotide as the active ingredient,
from 10 to 25% of a hydrosoluble co-solvent,
a pH modifier,
from 0 to 1% of an additive selected from stabilizers, antioxidants, surfactants, and mixtures thereof, and
water (qsp 100%),
the pH of the composition ranging from 4.0 to 6.0, the pH modifier being different from the hydrosoluble co-solvent.

In another preferred embodiment, the composition according to the invention is for a sustained release of an active ingredient for at least 2 months, consisting of:
from 35 to 55% of lanreotide as the active ingredient,
from 10 to 25% of a hydrosoluble co-solvent selected from NMP, low molecular PEG, glycofurol and mixtures thereof,
a pH modifier selected from acetic acid, citric acid, lactic acid, phosphoric acid, hydrochloric acid, stearic acid and pamoic acid,
from 0 to 5% of an additive selected from stabilizers, antioxidants, surfactants, and mixtures thereof, and
water (qsp 100%),
the pH of the composition ranging from 4.0 to 6.0.

In another preferred embodiment, the composition according to the invention is for a sustained release of an active ingredient for at least 2 months, consisting of:
from 35 to 55% of lanreotide as the active ingredient,
from 10 to 25% of a hydrosoluble co-solvent selected from NMP, low molecular PEG, glycofurol and mixtures thereof,
a pH modifier selected from acetic acid, citric acid, lactic acid, phosphoric acid, hydrochloric acid, stearic acid and pamoic acid,
from 0 to 1% of an antioxidant selected from methionine, histidine, tryptophan, glutathione, ascorbic acid, citric acid, disodium edetate, sodium metabisulfite, butylhydroxytoluene, butylhydroxyanisol, and mixtures thereof, and
water (qsp 100%),
the pH of the composition ranging from 4.0 to 6.0.

In a preferred embodiment, a pharmaceutical composition of the present invention is free of any non hydrosoluble, biocompatible and/or biodegradable, (co)polymer, and comprises or consisting essentially of or consisting of
lanreotide as the active ingredient,
acetic acid as pH modifier,
glycofurol as hydrosoluble co-solvent, and
water for injection,
the pH of the composition ranging from 4.0 to 6.0.

In another preferred embodiment, a pharmaceutical composition of the present invention is free of any non hydrosoluble, biocompatible and/or biodegradable, (co)polymer, and comprises or consisting essentially of or consisting of
lanreotide as the active ingredient,
acetic acid as pH modifier,
glycofurol as hydrosoluble co-solvent, and
water for injection,
the pH of the composition ranging from 4.0 to 6.0, and lanreotide being in an acetate form,
and more preferably comprises or consists essentially of or consisting of
from 40 to 50% (w/w) of lanreotide,
from 16 to 22% (w/w) of glycofurol, and
qsp 100% of water for injection.

In a particular embodiment, a pharmaceutical composition of the present invention is free of any non hydrosoluble, biocompatible and/or biodegradable, (co)polymer, and comprises or consists essentially of or consisting of
from 42 to 48% (w/w) of lanreotide,
from 16 to 22% (w/w) of glycofurol, from 5 to 7% (w/w) of acetic acid, and
qsp 100% of water for injection,
the pH of the composition ranging from 4.8 to 5.4, and lanreotide being in its acetate form.

In a particular embodiment, a pharmaceutical composition of the present invention is free of any non hydrosoluble, biocompatible and/or biodegradable, (co)polymer, and comprises or consists essentially of or consisting of
from 42 to 46% (w/w) of lanreotide,
from 16 to 20% (w/w) of glycofurol,
acetic acid, and
qsp 100% of water for injection,
the pH of the composition ranging from 4.8 to 5.4, lanreotide being in its acetate form, and glycofurol being of formula (1) as defined above or a mixture thereof.

In another particular embodiment, a pharmaceutical composition of the present invention is free of any non hydrosoluble, biocompatible and/or biodegradable, (co)polymer, and comprises or consists essentially of or consisting of
from 42 to 46% (w/w) of lanreotide,
from 16 to 20% (w/w) of glycofurol,
acetic acid, and
qsp 100% of water for injection,
the pH of the composition ranging from 4.8 to 5.4, lanreotide being in its acetate form, and glycofurol being of formula (1) as defined above wherein n is an integer from 1 to 2 or a mixture thereof.

In the case where lanreotide is in its acetate form and acetic acid is used as pH modifier, the acetate content in the composition, coming from lanreotide under its salt form and from acetic acid, can be measured.

When lanreotide is in its acetate form, acetic acid as pH modifier may be added in such a manner that the concentration of acetate content in the composition is ranging from 2 to 10% by weight, and preferably from 6 to 10% by weight relative to the total weight of the composition.

In another embodiment, a pharmaceutical composition of the present invention is free of any non hydrosoluble, biocompatible and/or biodegradable, (co)polymer, and comprises or consisting essentially of or consisting of
lanreotide in its acetate form,
acetic acid as pH modifier,
glycofurol as hydrosoluble co-solvent, and
water for injection,
the acetate content in the composition being ranged from 2 to 10% by weight, and preferably from 6 to 10% by weight, and more preferably
from 42 to 48% (w/w) of lanreotide,
from 16 to 22% (w/w) of glycofurol,
acetic acid, and
qsp 100% of water for injection,
the pH of the composition ranging from 4.8 to 5.4, and the acetate content in the composition being ranged from 6 to 10% by weight.

In another embodiment, a pharmaceutical composition of the present invention is free of any non hydrosoluble, biocompatible and/or biodegradable, (co)polymer, and comprises or consists essentially of or consisting of
lanreotide in its acetate form,
acetic acid as pH modifier,
glycofurol as hydrosoluble co-solvent, and
water for injection,
the acetate content in the composition being ranged from 2 to 10% by weight, and preferably from 6 to 10% by weight, and glycofurol being of formula (1) or a mixture thereof, and more preferably comprising or consisting essentially of or consisting of
from 42 to 48% (w/w) of lanreotide,
from 16 to 22% (w/w) of glycofurol,
acetic acid, and
qsp 100% of water for injection,
the pH of the composition ranging from 4.8 to 5.4, the acetate content in the composition being ranged from 6 to 10% by weight, and glycofurol being of formula (1) or a mixture thereof wherein n is an integer from 1 to 2, In another particular embodiment, a pharmaceutical composition of the present invention is free of any non hydrosoluble, biocompatible and/or biodegradable, (co)polymer, and comprises:
lanreotide as the active ingredient,
acetic acid as pH modifier,
glycofurol as hydrosoluble co-solvent,
an additive selected from stabilizers, antioxidants and surfactants, and
water for injection,
the pH of the composition ranging from 4.0 to 7.5, and lanreotide being in an acetate form.

In another preferred embodiment, the composition according to the invention is for a sustained release of an active ingredient for at least 2 months, consisting of:
from 35 to 55% of lanreotide as the active ingredient,
from 10 to 25% of a hydrosoluble co-solvent,
a pH modifier, and
water (qsp 100%),
the pH of the composition ranging from 4.0 to 7.5, more preferably from 4.0 to 6.0.

In another preferred embodiment, the composition according to the invention is for a sustained release of an active ingredient for at least 2 months, consisting of:
from 42 to 46% of lanreotide as the active ingredient,
from 16 to 20% of glycofurol of formula (1) as defined above, or a mixture thereof,
acetic acid as pH modifier,
from 0 to 5% of an additive selected from stabilizers, antioxidants, surfactants, and mixtures thereof, and
water (qsp 100%),
the pH of the composition ranging from 4.0 to 6.0.

In another preferred embodiment, the composition according to the invention is for a sustained release of an active ingredient for at least 2 months, consisting of:
from 42 to 46% of lanreotide as the active ingredient, in acetate form,
from 16 to 20% of glycofurol of formula (1) above wherein n is an integer from 1 to 2, or a mixture thereof,
acetic acid as pH modifier,
from 0 to 1% of an additive selected from stabilizers, antioxidants, surfactants, and mixtures thereof, and
water (qsp 100%),
the pH of the composition ranging from 4.8-5.4.

In another preferred embodiment, the composition according to the invention is for a sustained release of an active ingredient for at least 2 months, consisting of:
from 42 to 46% of lanreotide as the active ingredient, in acetate form,
from 16 to 20% of glycofurol of formula (1) above wherein n is an integer from 1 to 2, or a mixture thereof,
acetic acid as pH modifier,
from 0 to 1% of an antioxidant selected from methionine, histidine, tryptophan, glutathione, ascorbic acid, disodium edetate, citric acid, sodium metabisulfite, butylhydroxytoluene (BHT), butylhydroxyanisol, and mixtures thereof, and
water (qsp 100%),
the pH of the composition ranging from 4.8-5.4.

A pharmaceutical composition according to the present invention is a semi-solid formulation. A semi-solid composition can be injected using a standard device for injection such as a syringe connected to a needle. The viscosity and other physical state characteristics of the compositions can be assessed as the injectability, when the administration step is evaluated. The injectability can be determined conducting simulated injection tests and according to different physical methods. The injectability can be reported as injection strength or syringe injection force (SIF).

The SIF can be determined using a dynamometer (L1000R, Lloyd Instruments Ltd.) equipped with a calibrated cell (NLC 100N, Lloyd Instruments Ltd.). The pharmaceutical composition conditioned in a 4.5 mm diameter syringe coupled with a 20 mm length× 1.2 mm ID needle is tested for its injectability during a simulated discharge at a 100-200 mm/min speed range where the force applied by the instrument on the plunger and its displacement are recorded. The simulated injection is performed vertically in the air. The maximum injection force (in N) is derived from the data collected during the discharge.

In a preferred embodiment, a pharmaceutical composition according to the present invention presents an injectability defined by a SIF ranging from 5 to 50 N when tested with the method defined above with a dose up to 500 mg of lanreotide. Preferably the SIF of the pharmaceutical composition is ranging from 10 to 35 N.

A pharmaceutical composition according to the present invention is administered by the parenteral route. In a preferred embodiment, the composition of the present invention is administered by subcutaneous, intramuscular or deep-subcutaneous injection, and more preferably subcutaneous or deep-subcutaneous injection.

For the sub-cutaneous route, and deep-subcutaneous in particular, which remains the preferred one, the volume of injection is preferably not greater than 2 or 1.9 or 1.8 or 1.7 or 1.6 or 1.5 or 1.4 or 1.3 or 1.2 or 1.1. or 1 mL. In order to load up to 500 mg of lanreotide in such a volume, specific formulations had to be defined as the controlled-release properties had to be combined with the high concentration of active ingredient and an acceptable injectability. Such a situation is a challenge as a significant proportion of specific excipients aimed to provide the sustained release properties is usually required and this amount removes capacity of loading for the active ingredient.

A pharmaceutical composition according to the present invention allows a sustained release of lanreotide in humans for at least 2 months. Such release is obtained without any (co)polymeric matrix in the composition, in particular without any non hydrosoluble, biocompatible and/biodegradable, (co)polymeric agents usually used in sustained release composition such as polylactides (PLA), polyglycolides (PLG), poly lactide-co-glycolides (PLGA), polyalkylcyanoacrylates, poly-s-caprolactones and any (co)polymer agents obtained by combination or modification of these biocompatible (co)polymers.

In a preferred embodiment, the sustained release of lanreotide is of at least 2 to 6 months in humans.

In a preferred embodiment, the sustained release of lanreotide is of at least 2 months in humans.

In a preferred embodiment, the sustained release of lanreotide is of at least 3 months in humans.

The composition according to the invention allows a sustained release for at least 63 days, 70 days, 77 days, 84 days, or 90 days and preferably 91 days.

In a preferred embodiment, the composition according to the invention allows a sustained release for at least 63 days.

In another preferred embodiment, the composition according to the invention allows a sustained release for at least 70 days. In another preferred embodiment, the composition according to the invention allows a sustained release for at least 77 days. In a more preferred embodiment, the composition according to the invention allows a sustained release for at least 84 days. In another more preferred embodiment, the composition of the present invention allows a sustained release for at least 91 days.

Lanreotide is a marketed somatostatin analogue. It is indicated in the treatment of acromegaly due to both pituitary and non-pituitary growth hormone-secreting tumors, the management of symptoms caused by neuroendocrine tumors (NET), particularly carcinoid tumors and VIPomas, and in the treatment of thyrotrophic adenoma.

A pharmaceutical composition according to the present invention may be useful in the treatment of acromegaly due to both pituitary and non-pituitary growth hormone-secreting tumors, the management of symptoms caused by neuroendocrine tumors (NET), particularly carcinoid tumors and VIPomas, and in the treatment of thyrotrophic adenoma. In a preferred embodiment, a pharmaceutical composition according to the present invention is useful in the treatment of acromegaly or NET. The NET can e.g. be selected from functioning and non-functioning gastroenteropancreatic neuroendocrine tumors.

The invention therefore also relates to a method of treatment of a patient suffering from acromegaly by administering a therapeutically active amount of the pharmaceutical composition described in any one of the embodiments described above.

In an embodiment, the pharmaceutical composition in accordance with the present invention is administered or injected, or prepared for administration or injection into a patient in need thereof, no more frequently than every 8 weeks or preferably every 9 or 10 or 11 or 12 or 13 or 14 or 15 or 16 weeks. Preferably, it is administered or injected every 13 weeks.

In a further preferred embodiment, the pharmaceutical composition of the invention is administered or prepared for administration as a single injection.

Preferably, the method comprises administering the pharmaceutical composition at least once every 9 weeks or 10 weeks or 12 weeks or 13 weeks or 14 weeks or 15 weeks or 16 weeks. More preferably, the method comprises administering the pharmaceutical composition at least once every 13 weeks.

In another embodiment, the pharmaceutical composition is administered by single injection. Preferably, it is injected intramuscularly, subcutaneously or deep subcutaneously.

In yet another embodiment, the pharmaceutical composition is administered at a dose of 60, 90, 120 or 240 or 360 mg of active pharmaceutical ingredient, i.e. lanreotide. Preferably, the pharmaceutical composition is administered at a dose of 120, 240, or 360 mg of lanreotide.

The invention also relates to a method of treatment or prevention of a patient suffering from a neuroendocrine tumor (NET) by administering a therapeutically active amount of the pharmaceutical composition described in any one of the embodiments above. Preferably, symptoms caused by neuroendocrine tumors (NET) are being treated or prevented. In an embodiment, these symptoms are selected from flushing, diarrhea, and abdominal cramping.

The invention also relates to a method of treatment or prevention of a patient suffering from thyrotrophic adenoma by administering a therapeutically active amount of the pharmaceutical composition described in any one of the embodiments above.

The invention also relates to a pharmaceutical composition according to any one of the embodiments described above for use in medicine. In an embodiment, the pharmaceutical composition of the invention is for use in treating or preventing acromegaly. In a further embodiment, the pharmaceutical composition is for use in treating or preventing a neuroendocrine tumor (NET). The NET can e.g. be selected from functioning and nonfunctioning gastroenterointestinal neuroendocrine tumors. Preferably, the pharmaceutical composition is for use in treating or managing a symptom of a NET such as a symptom selected from flushing, diarrhea, and abdominal pain. In a further embodiment, the pharmaceutical composition of the invention is for use in treating or preventing a thyrotrophic adenoma. In a preferred embodiment, the present invention relates to a pharmaceutical composition as defined above for use in the treatment of acromegaly due to both pituitary and non-pituitary growth hormone-secreting tumors, said composition consisting of:
from 35 to 55% of lanreotide as the active ingredient,
from 10 to 25% of a hydrosoluble co-solvent,
a pH modifier,
from 0 to 5% of an additive selected from stabilizers, antioxidants, surfactants, and mixtures thereof, and
water (qsp 100%),
the pH of the composition ranging from 4.0 to 7.5, and the pH modifier being different from the hydrosoluble co-solvent.

In a preferred embodiment, the present invention also relates to a pharmaceutical composition as defined above for use in the the management of symptoms caused by neuroendocrine tumors (NET), said composition consisting of:
from 35 to 55% of lanreotide as the active ingredient,
from 10 to 25% of a hydrosoluble co-solvent,
a pH modifier,
from 0 to 5% of an additive selected from stabilizers, antioxidants, surfactants, and mixtures thereof, and
water (qsp 100%),
the pH of the composition ranging from 4.0 to 7.5, and the pH modifier being different from the hydrosoluble co-solvent.

In a preferred embodiment, the present invention relates to a pharmaceutical composition as defined above for use in the treatment of acromegaly due to both pituitary and non-pituitary growth hormone-secreting tumors, said composition consisting of:
from 42 to 46% (w/w) of lanreotide,
from 16 to 20% (w/w) of glycofurol of formula (1) as defined above,
acetic acid,
from 0 to 5% of an additive selected from stabilizers, antioxidants, surfactants, and mixtures thereof, and
qsp 100% of water for injection,
the pH of the composition ranging from 4.0 to 6.0.

In a preferred embodiment, the present invention also relates to a pharmaceutical composition as defined above for use in the management of symptoms caused by neuroendocrine tumors (NET), said composition consisting of:
from 42 to 46% (w/w) of lanreotide,
from 16 to 20% (w/w) of glycofurol of formula (1) as defined above,
acetic acid,
from 0 to 5% of an additive selected from stabilizers, antioxidants, surfactants, and mixtures thereof, and
qsp 100% of water for injection,
the pH of the composition ranging from 4.0 to 6.0.

In a preferred embodiment, the present invention relates to a pharmaceutical composition as defined above for use in the treatment of acromegaly due to both pituitary and non-pituitary growth hormone-secreting tumors, said composition consisting of:
from 42 to 46% (w/w) of lanreotide,
from 16 to 20% (w/w) of glycofurol of formula (1) as defined above and n is an integer from 1 to 2,
acetic acid,
from 0 to 1% of an additive selected from stabilizers, antioxidants, surfactants, and mixtures thereof, and
qsp 100% of water for injection,
the pH of the composition ranging from 4.8 to 5.4, and lanreotide being in its acetate form.

Figure 2:
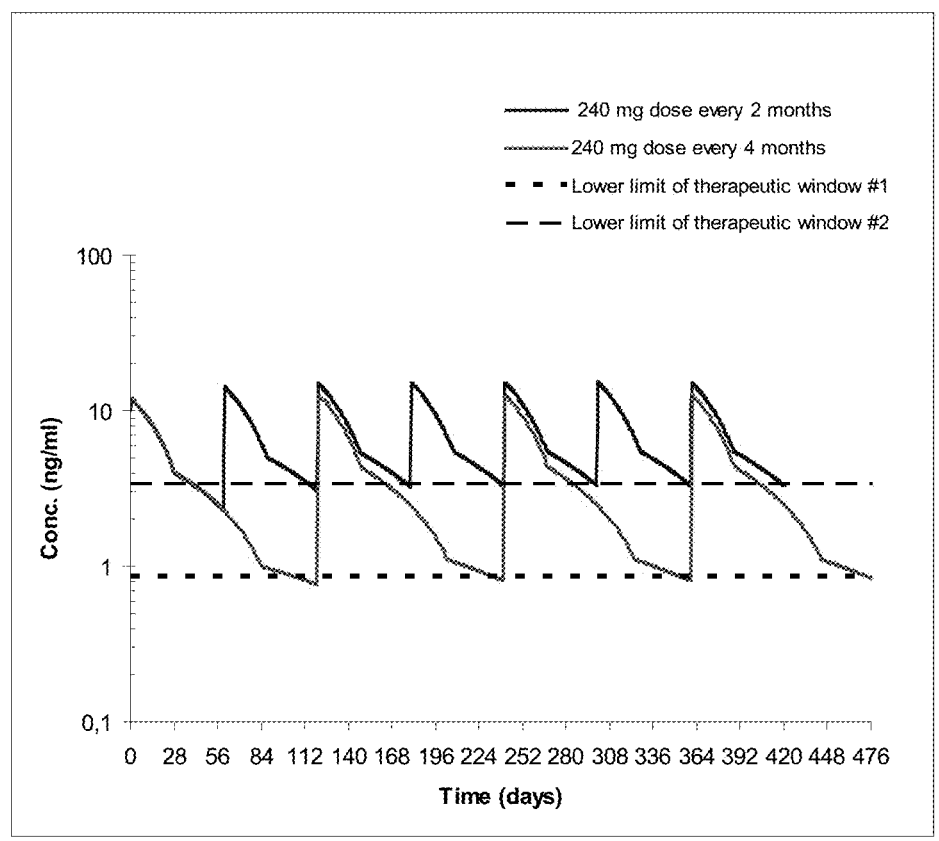
FIG. 2 depicts the pharmacokinetic profiles obtained following the administration of a 240 mg dose of lanreotide every 2 months and the administration of a 240 dose of lanreotide every 4 months, using a composition comprising lanreotide, glycofurol, acetic acid, and water.

In a preferred embodiment, the present invention also relates to a pharmaceutical composition as defined above for use in the management of symptoms caused by neuroendocrine tumors (NET), said composition consisting of:
from 42 to 46% (w/w) of lanreotide,
from 16 to 20% (w/w) of glycofurol of formula (1) as defined above and n is an integer from 1 to 2,
acetic acid,
from 0 to 1% of an additive selected from stabilizers, antioxidants, surfactants, and mixtures thereof, and
qsp 100% of water for injection,
the pH of the composition ranging from 4.8 to 5.4, and lanreotide being in its acetate form. A pharmaceutical composition according to the present invention provides after the first week of release a pharmacokinetic profile with a very constant and reproducible absorption rate and a specific negative slope which allow suitable scenarios when repeated administrations are applied to address chronic and long-term treatments. This specific pattern of pharmacokinetic profiles over a period of several weeks (FIG. 1) where the plasmatic levels of lanreotide decrease steadily, can be used to cover different durations of treatment and this for patients with different therapeutic windows. This modulation of the duration can be obtained using a single pharmaceutical composition at a defined and unique dose (FIG. 2).

The specific pharmacokinetic pattern is usually obtained from 2 weeks to 6 months and more preferably from 1 to 4 months. This allows defining new personalized treatments for patients and indications such as acromegaly and NET.

Furthermore the invention relates to a process for the preparation of a pharmaceutical composition for parenteral applications as described above.

Preferably, the invention relates to a process for the preparation of a pharmaceutical composition as described above, said process comprising the following steps:
preparation of a co-solvent mixture including the pH modifier and other additives when needed,
introduction of the active ingredient in a suitable container,
hydration of the active ingredient and homogenization of the composition by means of a mixing process at a temperature between 5 and 70° C., preferably at room temperature.

Preferably, the invention relates to a process for the preparation of a pharmaceutical composition for parenteral applications as described above, said process comprising the following steps:
preparation of a co-solvent mixture including the pH modifier and other additives when needed, and introduction of the mixture into a syringe or a syringe-like container, introduction of the active ingredient into a second syringe or a syringe-like container, connection of the 2 syringes or syringe-like containers with a 2-way connector, hydration of the active ingredient and homogenization of the composition by a kneading process between the 2 containers and through the connector at a temperature between 5° C. and 70° C., preferably at room temperature.

Preferably, the invention relates to a process for the preparation of a pharmaceutical composition for parenteral applications as described above, said process comprising the following steps:

preparation of a co-solvent mixture including the pH modifier and other additives if needed and introduction of the mixture into a syringe or a syringe-like container, introduction of the active ingredient into a second syringe or a syringe-like container, connection of the 2 syringes or syringe-like containers with a 3-ways connector fitted with a 2-way valve, removing the air from the system by a suitable method, for instance applying vacuum to the free port of the connector, hydration of the active ingredient and homogenization of the composition by a kneading process between the 2 containers and through the connector at a temperature between 5 and 70° C., preferably at room temperature.

In addition the whole preparation process can be controlled regarding the critical process parameters such as temperature, pressure, number of cycles and syringe-to-valve diameter ratio, with equipment common to the skilled practitioner.

Alternatively, the preparation of the pharmaceutical compositions as described above may be carried out extemporaneously, i.e. before administration.

In a preferred embodiment, the preparation of the pharmaceutical compositions as described above is carried out extemporaneously, i.e. before administration by a kneading process between:

a pre-filled syringe containing the suitable dose of active ingredient, and a syringe containing the mixture of the co-solvent, the optional pH modifier and other additives if needed (used as vehicle for reconstitution).

In a further embodiment of the invention, the active ingredient can be previously treated for instance by freeze-drying, drying, grinding, granulation, compaction, sieving, before the preparation of the pharmaceutical composition.

Any sterilization technique such as gamma irradiation, electron beam irradiation, steam or sterile filtration for part of the process can be used to obtain a sterile pharmaceutical composition.

In a further embodiment of the invention, the preparation of the pharmaceutical composition is conducted under aseptic conditions.

A pharmaceutical composition according to the present invention may be available as a pre-filled and ready-to-use presentation. It may also be available as a ready-to-reconstitute presentation where a freeze-dried product containing the active ingredient can be extemporaneously reconstituted with the mixture of the co-solvent, the optional pH modifier and other additives if needed as solvent for reconstitution.

As a further embodiment the pharmaceutical composition may be packaged in pre-filled syringes.

In a preferred embodiment, the present invention also relates to a pre-filled syringe, said syringe containing the pharmaceutical composition as define above for a sustained release of an active ingredient for at least 2 months and consisting of:

from 35 to 55% of lanreotide as the active ingredient,
from 10 to 25% of a hydrosoluble co-solvent,
a pH modifier,
from 0 to 5% of additive or mixture thereof selected from stabilizers, antioxidants and surfactants and
water (qsp 100%), the pH of the composition ranging from 4.0 to 7.5, and the pH modifier being different from the hydrosoluble co-solvent.

In another preferred embodiment, the present invention also relates to a pre-filled syringe, said syringe containing a pharmaceutical composition as defined above for a sustained release of an active ingredient for at least 2 months and consisting of:

from 42 to 46% (w/w) of lanreotide,
from 16 to 20% (w/w) of glycofurol of formula (1) as defined above,
acetic acid,
from 0 to 5% of an additive selected from stabilizers, antioxidants, surfactants, and mixtures thereof, and
qsp 100% of water for injection, the pH of the composition ranging from 4.0 to 6.0.

In another preferred embodiment, the present invention also relates to a pre-filled syringe, said syringe containing a pharmaceutical composition as defined above for a sustained release of an active ingredient for at least 2 months and consisting of:

from 42 to 46% (w/w) of lanreotide,
from 16 to 20% (w/w) of glycofurol of formula (1) as defined above and n is an integer from 1 to 2,
acetic acid,
from 0 to 1% of an additive selected from stabilizers, antioxidants, surfactants, and mixtures thereof, and
qsp 100% of water for injection, the pH of the composition ranging from 4.8 to 5.4, and lanreotide being in its acetate form.

In a preferred embodiment both freeze-dried product and solvent for reconstitution are packed in syringes which can be connected and used as a mixing device to facilitate the reconstitution process and the final administration of the reconstituted formulation.

Another subject of the present invention is a pharmaceutical composition for a sustained release of the active ingredient for at least 2 months, comprising, consisting essentially of or consisting of:

as the active ingredient, a hydrosoluble peptide or any pharmaceutically acceptable salt thereof,
glycofurol as co-solvent,
optionally a pH modifier, and
water, the pH of the composition ranging from 4.0 to 8.

Suitable peptides that can be used in the invention include growth hormone (GH), growth hormone releasing peptide (GHRP), growth hormone releasing factor (GRF), epidermal growth factor, interferon, insulin, somatostatin, bombesin, calcitonin, calcitonin gene related peptide (CGRP), amylin, parathyroid hormone (PTH), parathyroid hormone related peptide (PTHrp), gastrin, gastrin releasing peptide (GRP), melanocyte stimulating hormone (MSH), adrenocorticotrophic hormone (ACTH), luteinizing hormone (LH), luteinizing hormone-releasing hormone (LHRH), cytokinases, sorbine, cholecystokinin (CCK), glucagon, glucagon-like peptide (GLP), gastrin, enkephalin, neuromedin, endothelin, substance P, neuropeptide Y (NPY), peptide YY (PYY), vasoactive intestinal peptide (VIP), pituitary adenylate cyclase activating polypeptide (PACAP), bradykinin, thyrotropin releasing hormone (TRH), beta-cell tropin (a fragment of ACTH), or biologically active analogs of any of the foregoing.

The terms "biologically active analog" and "analog" are used interchangeably herein to cover naturally occurring, recombinant, and synthetic peptides, or derivatives or fragments of such peptides, that exhibit substantially the same agonist or antagonist effect of unmodified, or naturally occurring peptides, including e.g., those in which one or more of the naturally occurring amino acid residues has been deleted, substituted, or modified, or the N- or C-terminal group has been structurally modified. The agonist or antagonist effect of a peptide on its ligand or receptor can be measured e.g. in in vitro or in vivo assays, such as cell-based assays or experimental animal models adapted to the particular peptide. Such assays are well within the knowledge of the skilled person.

Preferred hydrosoluble peptide salts according to the present invention include salts of growth hormone (GH), growth hormone releasing peptide (GHRP), growth hormone releasing factor (GRF), insulin, somatostatin, parathyroid hormone (PTH), adrenocorticotrophic hormone (ACTH), luteinizing hormone (LH), luteinizing hormone-releasing hormone (LHRH) or gonadotropin-releasing hormone (GnRH), glucagon-like peptide (GLP), or biologically active analogs of any of the foregoing. In a more preferred embodiment, the hydrosoluble peptide salts according to the present invention include salts of growth hormone (GH), somatostatin, adrenocorticotrophic hormone (ACTH), luteinizing hormone-releasing hormone (LHRH), glucagon-like peptide (GLP), or biologically active analogs of any of the foregoing.

In another preferred embodiment, the active ingredient is a somatostatin analog selected from lanreotide, octreotide, pasireotide, or any pharmaceutically acceptable salt thereof In another preferred embodiment, the active ingredient is a LH-RH analog selected from avorelin, buserelin, deslorelin, gonadorelin, goserelin, histrelin, leuprorelin, lutrelin, nafarelin, peforelin, triptorelin, abarelix, cetrorelix, degarelix, detirelix, ganirelix, iturelix, ozarelix, prazarelix, ramorelix, teverelix, or any pharmaceutically acceptable salt thereof, and more preferably from buserelin, goserelin, leuprorelin, nafarelin, triptorelin, or any pharamaceutically acceptable salt thereof.

Pharmaceutically acceptable salts which can be used for the peptides in accordance with the present invention are preferably pharmaceutically acceptable salts of organic acids, such as those of acetic, phenylacetic, lactic, malic, pamoic, ascorbic, succinic, benzoic, methanesulphonic or toluenesulphonic acids, or pharmaceutically acceptable salts of inorganic acids, such as those of hydrochloric, hydrobromic, hydriodic, sulphuric or phosphoric acids.

In accordance with the present invention, such pharmaceutical compositions are preferably for use as a medicament or are used in a method of treating a disease in a patient in need thereof.

Another subject of the present invention is a pharmaceutical composition for a sustained release of the active ingredient for at least 2 months, comprising, consisting essentially of or consisting of:
as the active ingredient, a hydrosoluble peptide selected from lanreotide, octreotide, pasireotide, buserelin, goserelin, leuprorelin, nafarelin and triptorelin, or any pharmaceutically acceptable salt thereof,
glycofurol as co-solvent,
optionally a pH modifier, and
water,
the pH of the composition ranging from 4.0 to 8,
and preferably comprising, consisting essentially of or consisting of:
as the active ingredient, a hydrosoluble peptide selected from lanreotide, octreotide, pasireotide, buserelin, goserelin, leuprorelin, nafarelin and triptorelin, or any pharmaceutically acceptable salt thereof,
glycofurol as co-solvent,
a pH modifier, and
water, Advantageously, the peptide or its pharmaceutically acceptable salt is present in a concentration ranging from 20 to 60, preferably from 35 to 55% by weight, and more preferably from 40 to 50% by weight, relative to the total weight of the composition.

In a preferred embodiment, the glycofurol is present in a concentration ranging from 10 to 35% by weight, and more preferably from 10 to 25% by weight relative to the total weight of the composition.

In accordance with the present invention, such pharmaceutical compositions are preferably for use as a medicament or are used in a method of treating a disease in a patient in need thereof.

Another subject of the present invention is a pharmaceutical composition for a sustained release of the active ingredient for at least 2 months, comprising or consisting essentially of or consisting of:
as the active ingredient, a hydrosoluble peptide selected from lanreotide, octreotide, pasireotide, buserelin, goserelin, leuprorelin, nafarelin and triptorelin, or any pharmaceutically acceptable salt thereof, present in a concentration ranging from 20 to 60% by weight, relative to the total weight of the composition,
glycofurol as co-solvent, present in a concentration ranging from 10 to 35% by weight relative to the total weight of the composition
a pH modidier, and
water,
the pH of the composition ranging from 4.0 to 8.

In accordance with the present invention, such pharmaceutical compositions are preferably for use as a medicament or are used in a method of treating a disease in a patient in need thereof.

Unless otherwise indicated, all technical and scientific terms used herein have the same meaning as commonly understood by a specialist in the domain associated with this invention.

The following examples are presented to illustrate the above procedures and should not be considered as limiting the scope of the invention.

EXPERIMENTAL PART

1—Preparation Process

Example 1a

Different batches are prepared using an acetate salt of lanreotide as active pharmaceutical ingredient (API). The required amount of lanreotide acetate is hydrated and homogenized with the corresponding mixture of water for injection (WFI)/NMP/acetic acid in a suitable container.

Both acetate and water contents of the formulation are adjusted taking into account the contribution of the API which also contains these 2 components.

Once homogeneous media are obtained, the different formulations are aliquoted in syringes suitable for pre-filled product and preferably compatible with a terminal sterilization using gamma-irradiation.

Part of the individual doses obtained at the end of the filling step are sterilized by gamma-irradiation (dose >25 kGy).

Several formulations according to the invention are thus prepared. The information related to these examples is compiled in Table 1.

TABLE 1

| Batch | Content % (w/w) | | | |
|---|---|---|---|---|
| | Lanreotide | Acetate | NMP | WFI |
| B1 | 46.7 | q.s. 7.5 | 16.9 | q.s. 100 |
| B2 | 47.1 | q.s. 7.5 | 16.9 | q.s. 100 |
| B3 | 41.8 | q.s. 6.5 | 17.0 | q.s. 100 |
| B4 | 38.1 | q.s. 6.1 | 17.4 | q.s. 100 |
| B5 | 44.6 | q.s. 6.2 | 16.4 | q.s. 100 |
| B6 | 50.8 | q.s. 6.3 | 15.6 | q.s. 100 |
| B7 | 39.8 | q.s. 5.0 | 17.4 | q.s. 100 |
| B8 | 47.2 | q.s. 6.3 | 21.8 | q.s. 100 |
| B9 | 49.6 | q.s. 7.7 | 15.6 | q.s. 100 |
| B10 | 47.6 | q.s. 7.7 | 21.8 | q.s. 100 |
| B11 | 38.9 | q.s. 6.2 | 12.5 | q.s. 100 |
| B12 | 47.8 | q.s. 7.4 | 14.9 | q.s. 100 |
| B13 | 46.9 | q.s. 7.4 | 18.9 | q.s. 100 |
| B14 | 43.6 | q.s. 6.8 | 17.0 | q.s. 100 |
| B15 | 39.6 | q.s. 6.2 | 15.0 | q.s. 100 |
| B16 | 39.8 | q.s. 6.2 | 19.1 | q.s. 100 |

Example 1 b

A pharmaceutical composition using dual-syringe system is prepared as follows:

1.966 grams of a WFI:NMP [60:40] v/v mixture are introduced in a 5 mL plastic syringe.

3.033 grams of lanreotide acetate are introduced in 20 mL plastic syringe fitted with a 2-way connector. The syringe containing the liquid mixture is connected to the free port of the connector to initiate hydration of the active ingredient. The homogenization of the formulation is achieved by a push-pull kneading process between the 2 syringes and through the connector. Once the active ingredient is hydrated, the whole product is kept in the 5 mL syringe and the 20 mL syringe is replaced by a new empty 5 mL syringe for the final stage of the mixing process.

Once homogeneous, the formulation is collected in one of the two 5 mL syringes and then filled in 1 mL plastic syringes fitted with a 1.2 mm internal diameter (ID)*20 mm length (L) needle, to a 240 mg lanreotide dose. The needle is then capped with a needle shield.

The individual doses filled in the syringes are sealed in aluminium bags and gamma-irradiated (dose >25 kGy).

Example 1c

A pharmaceutical composition using dual-syringe system and vacuum is prepared as follows:

32.73 grams of WFI are mixed with 22.86 grams of NMP and 4.32 grams of acetic acid in a glass bottle. 30.55 grams of the mixture are transferred in a 250 mL stainless steel syringe.

38.06 grams of lanreotide acetate are introduced into a 250 mL stainless steel syringe. Using a plastic plunger and a spatula, the active ingredient introduced in the syringe is gently compacted.

Both syringes are fitted with a 3-way valve. Vacuum is applied to the syringe containing the active ingredient to a value lower or equal to 0.600 mbar during 30 min, using a pump connected via the 3-way valve.

Then, the valve is commuted to connect both syringes and initiate the hydration of the active ingredient. The homogenization of the formulation is achieved by a push-pull kneading process between the 2 syringes and through the valve.

When a homogeneous mixture is obtained, the formulation is collected in one of the two 250 mL syringes and then filled in 1.0 mL plastic syringes fitted with a 1.2 mm internal diameter (ID)*20 mm length (L) needle, to a 360 mg lanreotide dose. The syringes are then capped with a needle shield.

57 individual doses of 360 mg of lanreotide are prepared.

The individual doses filled in the syringes are sealed in aluminium bags and gamma-irradiated (dose >25 kGy).

Example 1d

A pharmaceutical composition using dual-syringe system and vacuum is prepared as follows:

78.82 grams of WFI are mixed with 51.12 grams of NMP and 8.88 grams of acetic acid in a glass beaker. 94.27 grams of the mixture are transferred into a 750 mL stainless steelsyringe.

110.14 grams lanreotide acetate are introduced in a 750 mL stainless steelsyringe. Using a specific rod and a spatula the active ingredient introduced in the syringe is gently compacted Both syringes are fitted with a 3-way valve. Vacuum is applied to the syringe containing the active ingredient to a value lower than or equal to 0.600 mbar during 35 min, using a pump connected via the 3-way valve.

Then, the valve is commuted to connect both syringes and initiate the hydration of the active ingredient. The homogenization of the formulation is achieved by a push-pull kneading process between the 2 syringes and through the valve.

When a homogeneous mixture is obtained, the formulation is collected in one of the two 750 mL syringes and then filled in 1.0 mL plastic syringes fitted with a luer-lock 1.2 mm internal diameter (ID)*20 mm length (L) needle, to a 360 mg lanreotide dose. The syringes are then capped with a needle shield.

197 individual doses of 360 mg of lanreotide are thus prepared.

The individual doses filled in the syringes are sealed in aluminium bags and treated by gamma-irradiation (dose >25 kGy).

Example 1e

A pharmaceutical composition using both pre-mixing and dual-syringe system is prepared as follows:

8.445 grams of a WFI/NMP [10:90] v/v mixture is weighed in a glass beaker and 29.50 grams of lanreotide acetate are weighed in another glass beaker. 20 grams of lanreotide acetate are added to the solvent while gently mixing with a spatula. Then, 12.15 grams of a WFI:NMP [95:5] v/v mixture are weighed in a glass beaker and around 5 grams of lanreotide acetate are added to the previous product and mixed with a spatula. Then, the rest of lanreotide acetate (up to 29.50 grams) is added while gently mixing with a spatula, and the rest of the WFI:NMP [95:5]

v/v mixture (up to 12.15 g) are added and mixed with a spatula. An overage of 1% is applied for weighing the solvents.

This hydrated product is transferred in a 50 mL stainless steel syringe. This syringe is connected to another 50 mL stainless steel syringe by means of a connector. The homogenization of the formulation is achieved by a push-pull kneading process between the 2 syringes and through the connector.

Once homogeneous, the formulation is collected in one of the two 50 mL syringes and therefore aliquoted in 1 mL plastic syringes coupled with a 1.2 mm ID*20 mm L needle. The needle is capped with a needle shield. Individual doses of 240 mg of lanreotide are prepared.

The individual doses filled in the syringes are sealed in aluminium bags and gamma-irradiated (dose >25 kGy).

Example 1f

A pharmaceutical composition suitable for extemporaneous reconstitution is prepared as follows:

10.38 grams of lanreotide acetate are introduced in a 150 mL stainless steel syringe. 24.63 grams of acetic acid 0.2N is introduced into another 150 mL stainless steel syringe.

The syringe containing the active ingredient is fitted with a 2-way valve and vacuum is applied during 30 min using a pump. Once a vacuum lower than or equal to 0.600 mBar is reached, the syringe containing the 0.2N acetic acid is fitted with the free port of the valve. The valve is then opened to connect both syringes and initiate hydration of the active ingredient. The homogenization of the formulation is achieved by a push-pull kneading process between the 2 syringes and through the valve.

Once homogeneous, the formulation is collected in one of the two syringes and therefore aliquoted in 2.5 mL plastic syringes suitable for freeze-drying process and fitted with a Luer-lock tip.

Individual doses of 500 mg of lanreotide are prepared.

The uncapped syringes are freeze-dried in order to obtain a solid cake of lanreotide in powder form.

After freeze-drying, the individual doses are stoppered with a Luer-lock stopper, and sealed in an aluminium bag and gamma-irradiated (dose >25 kGy).

In parallel, the vehicle for reconstitution is prepared: 6.40 grams of WFI are mixed with 3.60 grams of NMP in a volumetric flask. The solution is then aliquoted in 3.0 mL plastic syringes compatible with the ones used for the freeze-dried product in terms of syringe-to-syringe connectivity.

The individual doses of the final formulation are prepared as follows:
connection of the 2 syringes,
hydration and homogenization by means of push-pull kneading process between the 2 syringes,
collection of the formulation in 1 of the 2 syringes,
disconnection of the 2 syringes and coupling of a Luer Lock needle for administration.

Example 1q

A pharmaceutical composition using a dual-syringe system and vacuum is prepared as follows:

103.35 grams of WFI are mixed with 83.70 grams of glycofurol and 12.95 grams of acetic acid in a glass bottle. 26.38 grams of the mixture are transferred in a 250 mL stainless steel syringe.

31.72 grams of lanreotide acetate are introduced in a 250 mL stainless steel syringe. Using a plastic plunger and a spatula, the active ingredient introduced in the syringe is gently compacted.

Both syringes are fitted with a 3-way valve. Vacuum is applied to the syringe containing the active ingredient using a pump connected via the 3-way valve.

Vacuum is applied during 190 min to reach a value lower than or equal to 0.500 mBar. Then, the valve is commuted to connect both syringes and initiate the hydration of the active ingredient. The homogenization of the formulation is achieved by a push-pull kneading process between the 2 syringes and through the valve.

Once homogeneous, the formulation is collected in one of the two 250 mL syringes and then filled in 1.2 mL plastic syringes with a 240 mg dose of Lanreotide. The syringes are capped with a needle shield.

68 individual doses of 240 mg of lanreotide having a pH of 5.0 are prepared.

This composition according to the present invention presents a maximum injection force defined by a SIF of 27 N at a 110 mm/min speed when tested with the method defined above with a dose of 240 mg of lanreotide.

The individual doses filled in the syringes are sealed in aluminum bags and gamma-irradiated (dose >25 kGy).

Example 1h

A pharmaceutical composition using a dual-syringe system and vacuum is prepared as follows:

127.02 grams of WFI are mixed with 61.88 grams of glycofurol and 11.09 grams of acetic acid in a glass bottle. 36.79 grams of the mixture are transferred in a 250 mL stainless steel syringe.

32.21 grams of lanreotide acetate are introduced in a 250 mL stainless steel syringe. Using a plastic plunger and a spatula, the active ingredient introduced in the syringe is gently compacted Both syringes are fitted with a 3-way valve. Vacuum is applied to the syringe containing the active ingredient using a pump connected via the 3-way valve.

Vacuum is applied during 120 min to reach a value lower than or equal to 0.500 mBar. Then, the valve is commuted to connect both syringes and initiate the hydration of the active ingredient. The homogenization of the formulation is achieved by a push-pull kneading process between the 2 syringes and through the valve.

Once homogeneous, the formulation is collected in one of the two 250 mL syringes and then filled in 1.2 mL plastic syringes with a 240 mg Lanreotide dose. The syringes are then capped with a needle shield.

75 individual doses of 240 mg of lanreotide having a pH of 4.9 are prepared.

This composition according to the present invention presents a maximum injection force defined by a SIF of 29 N at a 110 mm/min speed when tested with the method defined above with a dose of 240 mg of lanreotide.

The individual doses filled in the syringes are sealed in aluminum bags and gamma-irradiated (dose >25 kGy).

Example 1i

A pharmaceutical composition using dual-syringe system and vacuum is prepared as follows:

10.61 grams of WFI are mixed with 7.64 grams of PEG 600 and 1.75 grams of acetic acid in a glass bottle. 15.52 grams of the mixture are transferred in a 250 mL stainless steel syringe.

13.38 grams of lanreotide acetate are introduced in a 250 mL stainless steel syringe. Using a plastic plunger and a spatula, the active ingredient introduced in the syringe is gently compacted Both syringes are fitted with a 3-way valve. Vacuum is applied to the syringe containing the active ingredient using a pump connected via the 3-way valve.

Vacuum is applied during 30 min to reach a value lower than or equal to 0.600 mBar. Then, the valve is commuted to connect both syringes and initiate the hydration of the active ingredient. The homogenization of the formulation is achieved by a push-pull kneading process between the 2 syringes and through the valve.

Once homogeneous, the formulation is collected in one of the two 250 mL syringes and therefore aliquoted in 1.2 mL plastic syringes. The syringes are capped with a rubber stopper.

19 individual doses of 240 mg of lanreotide having a pH of 4.84 are prepared.

This composition according to the present invention presents a maximum injection force defined by a SIF of 61.9 N at a 175 mm/min speed when tested with the method defined above with a dose of 240 mg of lanreotide, and a SIF of 24 N at a 175 mm/min speed when tested with the method defined above with a dose of 60 mg of lanreotide.

The individual doses filled in the syringes are sealed in aluminum bags and gamma-irradiated (dose >25 kGy).

Example 1j

A pharmaceutical composition using dual-syringe system and vacuum is prepared as follows:

11.51 grams of WFI are mixed with 6.88 grams of PEG 600 and 1.61 grams of acetic acid in a glass bottle. 17.79 grams of the mixture are transferred in a 250 mL stainless steel syringe.

12.71 grams of lanreotide acetate are introduced in a 250 mL stainless steel syringe. Using a plastic plunger and a spatula, the active ingredient introduced in the syringe is gently compacted.

Both syringes are fitted with a 3-way valve. Vacuum is applied to the syringe containing the active ingredient using a pump connected via the 3-way valve.

Vacuum is applied during 30 min to reach a value lower than or equal to 0.600 mBar. Then, the valve is commuted to connect both syringes and initiate the hydration of the active ingredient. The homogenization of the formulation is achieved by a push-pull kneading process between the 2 syringes and through the valve.

Once homogeneous, the formulation is collected in one of the two 250 mL syringes and therefore aliquoted in 1.2 mL plastic syringes. The syringes are capped with a rubber stopper.

19 Individual doses of 240 mg of lanreotide having a pH of 4.68 are prepared.

This composition according to the present invention presents a maximum injection force defined by a SIF of 29.7 N at a 175 mm/min speed when tested with the method defined above with a dose of 240 mg of lanreotide, and a SIF of 15.6 N at a 175 mm/min speed when tested with the method defined above with a dose of 60 mg of lanreotide.

The individual doses filled in the syringes are sealed in aluminum bags and gamma-irradiated (dose >25 kGy).

Example 1k

A pharmaceutical composition using dual-syringe system and vacuum is prepared as follows:

18.19 grams of WFI are mixed with 9.27 grams of PEG 600 and 2.54 grams of acetic acid in a glass bottle. 20.42 grams of the mixture are transferred in a 250 mL stainless steel syringe.

14.58 grams of lanreotide acetate are introduced in a 250 mL stainless steel syringe. Using a plastic plunger and a spatula, the active ingredient introduced in the syringe is gently compacted.

Both syringes are fitted with a 3-way valve. Vacuum is applied to the syringe containing the active ingredient using a pump connected via the 3-way valve.

Vacuum is applied during 30 min to reach a value lower than or equal to 0.600 mBar. Then, the valve is commuted to connect both syringes and initiate the hydration of the active ingredient. The homogenization of the formulation is achieved by a push-pull kneading process between the 2 syringes and through the valve.

Once homogeneous, the formulation is collected in one of the two 250 mL syringes and therefore aliquoted in 1.2 mL plastic syringes. The syringes are capped with a rubber stopper.

24 individual doses of 240 mg of lanreotide having a pH of 4.65 are prepared.

This composition according to the present invention presents a maximum injection force defined by a SIF of 34.7 N at a 175 mm/min speed when tested with the method defined above with a dose of 240 mg of lanreotide, and a SIF of 19.9 N at a 175 mm/min speed when tested with the method defined above with a dose of 60 mg of lanreotide.

The individual doses filled in the syringes are sealed in aluminum bags and gamma-irradiated (dose >25 kGy).

Example 1l

A pharmaceutical composition using a dual-syringe system is prepared as follows:

0.09 grams of methionine are dissolved in 9.74 grams of WFI in a glass bottle. 8.44 grams of glycofurol and 1.73 grams of acetic acid are added to the solution. 4.28 grams of the mixture are transferred in a 20 mL stainless steel syringe.

5.22 grams of lanreotide acetate are introduced in a 20 mL stainless steelsyringe. Using a plastic plunger and a spatula, the active ingredient introduced in the syringe is gently compacted.

Both syringes are fitted with a 3-way valve. Vacuum is applied to the syringe containing the active ingredient using a pump connected via the 3-way valve.

Vacuum is applied during 30 min to reach a value lower than or equal to 0.500 mBar. Then, the valve is commuted to connect both syringes and initiate the hydration of the active ingredient. The homogenization of the formulation is achieved by a push-pull kneading process between the 2 syringes and through the valve.

Once homogeneous, the formulation is collected in one of the two 20 mL syringes and then filled in 1.2 mL plastic syringes with a 240 mg dose of lanreotide. The syringes are capped with a needle shield.

13 individual doses of 240 mg of lanreotide having a pH of 5.11 are prepared.

This composition according to the present invention presents a maximum injection force defined by a SIF of 24 N at a 110 mm/min speed when tested with the method defined above with a dose of 240 mg of lanreotide.

The individual doses filled in the syringes are sealed in aluminum bags and gamma-irradiated (dose >25 kGy).

Example 1m

Two batches of a pharmaceutical composition (B17 and B18) using a dual-syringe system and vacuum is prepared as follows.

Batch B17

A first sub-batch is prepared.

122.83 grams of WFI are mixed with 87.19 grams of glycofurol and 16.53 grams of acetic acid in a glass bottle. 113.19 grams of the mixture are transferred in a 750 mL stainless steel syringe.

122.20 grams of lanreotide acetate are introduced in a 750 mL stainless steel syringe. Using a plastic plunger and a spatula, the active ingredient introduced in the syringe is gently compacted Both syringes are fitted with a 3-way valve. Vacuum is applied to the syringe containing the active ingredient using a pump connected via the 3-way valve.

Vacuum is applied during 120 min to reach a value lower or equal to 0.500 mBar. Then, the valve is commuted to connect both syringes and initiate the hydration of the active ingredient. The homogenization of the formulation is achieved by a push-pull kneading process between the 2 syringes and through the valve.

Once homogeneous, the formulation is collected in one of the two 750 mL syringes.

A second sub-batch is prepared:

122.80 grams of WFI are mixed with 87.01 grams of glycofurol and 16.53 grams of acetic acid in a glass bottle. 113.19 grams of the mixture are transferred in a 750 mL stainless steel syringe.

122.40 grams of lanreotide acetate are introduced in a 750 mL stainless steel syringe. Using a plastic plunger and a spatula, the active ingredient introduced in the syringe is gently compacted Both syringes are fitted with a 3-way valve. Vacuum is applied to the syringe containing the active ingredient using a pump connected via the 3-way valve.

Vacuum is applied during 120 min to reach a value lower or equal to 0.500 mBar. Then, the valve is commuted to connect both syringes and initiate the hydration of the active ingredient. The homogenization of the formulation is achieved by a push-pull kneading process between the 2 syringes and through the valve.

Once homogeneous, the formulation is collected in one of the two 750 mL syringes.

Both sub-batches are mixed and homogenised by a push-pull kneading process between the 2 syringes through the valve and then filled in 1.2 mL plastic syringes with a 450 mg lanreotide dose. The syringes are then capped with a needle shield.

279 individual doses of 450 mg of lanreotide having a pH of 4.9 are prepared.

This composition according to the present invention presents a maximum injection force defined by a SIF of 20 N at a 110 mm/min speed when tested with the method defined above with a dose of 450 mg of lanreotide.

The individual doses filled in the syringes are sealed in aluminum bags and gamma-irradiated (dose >25 kGy).

Batch B18

121.73 grams of WFI are mixed with 86.40 grams of glycofurol and 16.41 grams of acetic acid in a glass bottle. 112.32 grams of the mixture are transferred in a 750 stainless steel syringe.

121.30 grams of lanreotide acetate are introduced in a 750 mL stainless steel syringe. Using a plastic plunger and a spatula, the active ingredient introduced in the syringe is gently compacted.

Both syringes are fitted with a 3-way valve. Vacuum is applied to the syringe containing the active ingredient using a pump connected via the 3-way valve.

Vacuum is applied during 120 min to reach a value lower or equal to 0.500 mBar. Then, the valve is commuted to connect both syringes and initiate the hydration of the active ingredient. The homogenization of the formulation is achieved by a push-pull kneading process between the 2 syringes and through the valve.

Once homogeneous, the formulation is collected in one of the two 750 mL syringes and then filled in 1.2 mL plastic syringes with a 270 mg Lanreotide dose. The syringes are then capped with a needle shield.

278 individual doses of 270 mg of lanreotide having a pH of 4.9 are prepared.

This composition according to the present invention presents a maximum injection force defined by a SIF of 16 N at a 110 mm/min speed when tested with the method defined above with a dose of 270 mg of lanreotide.

The individual doses filled in the syringes are sealed in aluminum bags and gamma-irradiated (dose >25 kGy).

2—Pharmacokinetic (PK) Studies

Example 2a

The pharmaceutical composition identified as B1 in Example 1a is injected in dog at a dose of 240 mg of lanreotide.

A total of six male Beagle dogs 16-23 kg bodyweight are used at the beginning of the study. They are maintained with free access to a dry standard diet and to drinkable water. The animals are subcutaneously administered in the inter scapular area by trained personnel.

Blood samples are obtained, through the cephalic veins, before injection (time 0), 15 and 30 minutes, 1, 2, 4, 8 and 10 hours, 1, 2, 3, 7, 10, 14, 21 and 28 days, and then once every 9-11 days (including if possible 56 and 84 days) until completing the experiment when lanreotide levels are undetected.

The blood samples remain at room temperature for a minimum of 30 min and then they are centrifuged (1600 g for 20 min at 4° C.) in the centrifuge.

The lanreotide serum concentration is determined by means of a validated Radio Immuno Assay (RIA) method that implies the preparation of calibrated standard curves and the inclusion of quality control samples. The limit of quantification is 80 pg·ml-1.

A non-compartmental pharmacokinetic analysis of the individual serum concentration-actual time profile is applied by means of the WinNonlin v5.2 software in order to obtain at least the following parameters: peak serum concentration (Cmax), time to peak (Tmax), area under the time-concentration curve from 0 to t (AUCt) and mean residence time from 0 to t (MRTt).

Figure 3:
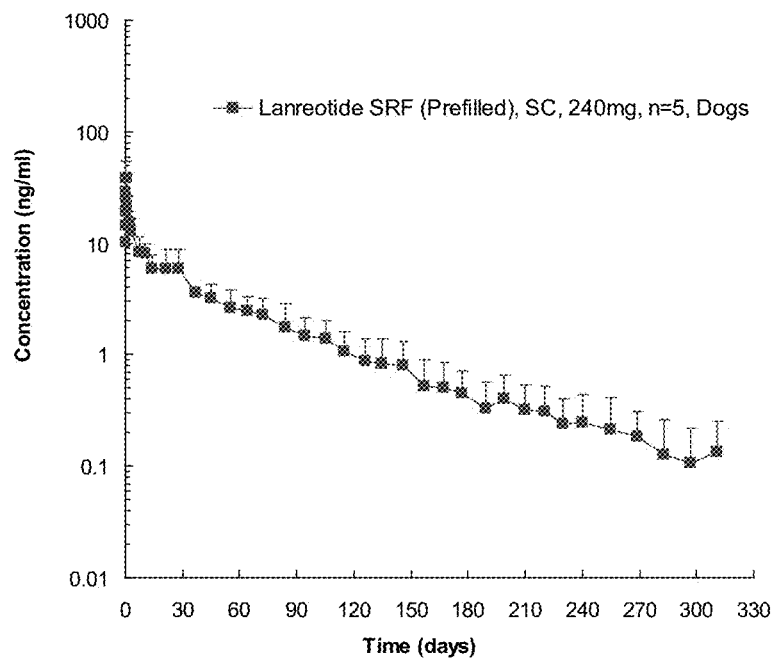
FIG. 3 depicts the pharmacokinetic profile obtained following the administration of a 240 mg dose of lanreotide using a composition comprising 46.7% (w/w) lanreotide, 16.9% (w/w) N-methyl-2-pyrrolidone, acetate, and water.

Resulting mean±SD (standard deviation) pharmacokinetic profiles obtained in dogs are presented in the FIG. 3. This PK study demonstrates the sustained release (SR) properties of this composition.

Example 2b

The pharmaceutical composition containing 32.9% of lanreotide and 40.2% of propylene glycol [acetate and WFI q.s. 100%] is injected in dog at a dose of 60 mg of lanreotide.

A total of three male Beagle dogs 16-23 kg bodyweight are used. They are maintained with free access to a dry standard diet and to drinkable water. The animals are subcutaneously administered in inter scapular area by trained personnel.

Blood samples are obtained, through the cephalic veins, before injection (time 0), 15 and 30 minutes, 1, 2, 4, 8 and 10 hours, 1, 2, 3, 7, 10, 14, 17, 21, 24 and 28 days, and then once every 9-11 days (including if possible 56 and 84 days) until completing the experiment when lanreotide levels are undetected.

The blood samples remains at room temperature for a minimum of 30 min and then they are centrifuged (1600 g for 20 min at 4° C.) in the centrifuge.

The lanreotide serum concentration is determined by means of a validated RIA method that implies the preparation of calibrated standard curves and the inclusion of quality control samples. The limit of quantification is 80 pg·ml-1.

A non-compartmental pharmacokinetic analysis of the individual serum concentration-actual time profile is applied by means of the WinNonlin v5.2 software in order to obtain at least the following parameters: peak serum concentration (Cmax), time to peak (Tmax), area under the time-concentration curve from 0 to t (AUCt) and mean residence time from 0 to t (MRTt).

Figure 4:
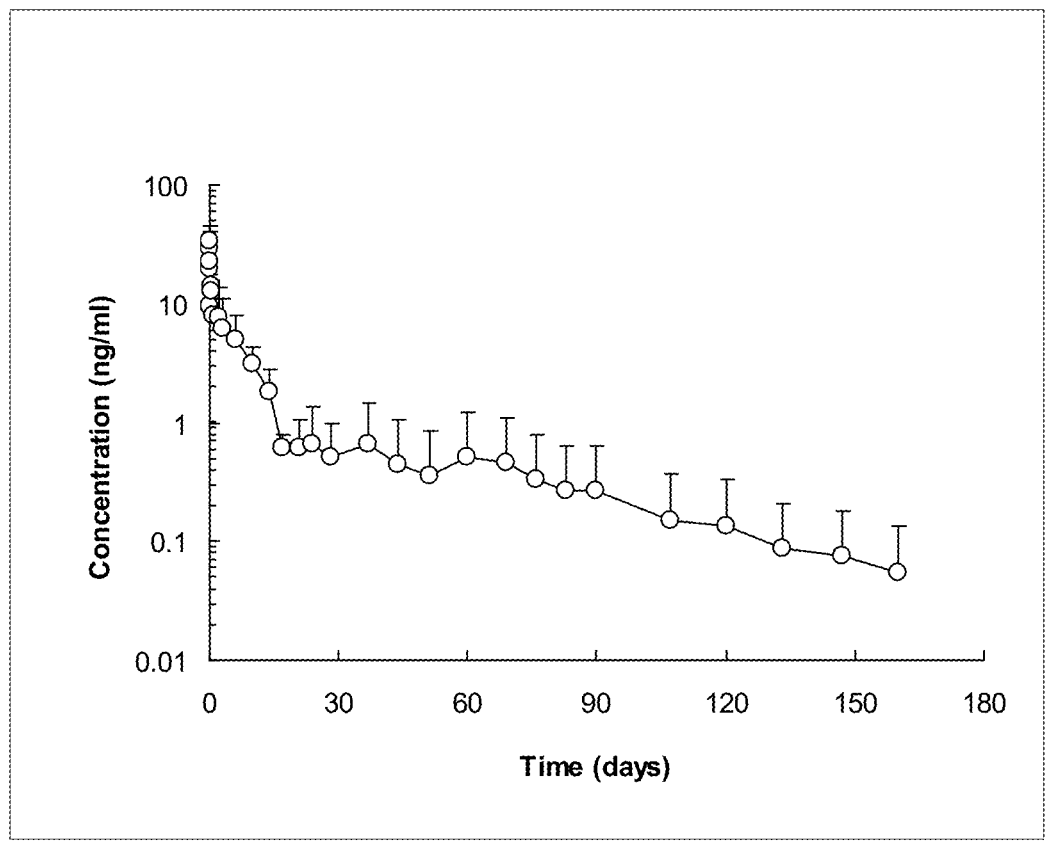
FIG. 4 depicts the pharmacokinetic profile obtained following the administration of a 60 mg dose of lanreotide using a composition comprising 32.9% lanreotide, 40.2% propylene glycol, acetate, and water.

Resulting mean±SD pharmacokinetic profiles obtained in dogs are presented in the FIG. 4. This PK study demonstrates the sustained release (SR) properties of this composition.

Example 2c

The pharmaceutical compositions identified in Examples 1g (G1) and 1h (G2) are injected in dog at a dose of 240 mg of lanreotide. These compositions are reported in Table 2.

TABLE 2

| Composition | Content % (w/w) | | | |
|---|---|---|---|---|
| | Lanreotide | Acetate | Glycofurol | WFI |
| G1 | 47.50 | q.s. 7.50 | 19.00 | q.s. 100.00 |
| G2 | 40.00 | q.s. 7.25 | 16.50 | q.s. 100.00 |

A total of 12 Beagle dogs (six males and six females) 9-14 kg bodyweight per formulation are used at the beginning of the study. They are maintained with free access to a dry standard diet and to drinkable water. The animals are subcutaneously administered in inter scapular area by trained personnel.

Blood samples are obtained from unanesthetized animals by direct venipuncture from the jugular vein, before injection (time 0), 15 and 30 minutes, 1, 2, 4, 8 and 12 hours, 1, 1.5, 2, 2.5, 3, 4, 5, 7, 10, 14, 21, 28, 35, 42, 49, 56, 63, 70, 77, 84, 90, 105, 119, 135, 150, 165 and 180 days after administration.

The blood samples remain at room temperature for a minimum of 30 min and then they are centrifuged (1600 g for 20 min at 4° C.) in the centrifuge.

The lanreotide serum concentration is determined by means of a validated RIA method that implies the preparation of calibrated standard curves and the inclusion of quality control samples. The limit of quantification is 80 pg·ml-1.

A non-compartmental pharmacokinetic analysis of the individual serum concentration-actual time profile is applied by means of the WinNonlin v5.2 software in order to obtain at least the following parameters: peak serum concentration (Cmax), time to peak (Tmax), area under the time-concentration curve from 0 to t (AUCt) and mean residence time from 0 to t (MRTt).

Figure 5:
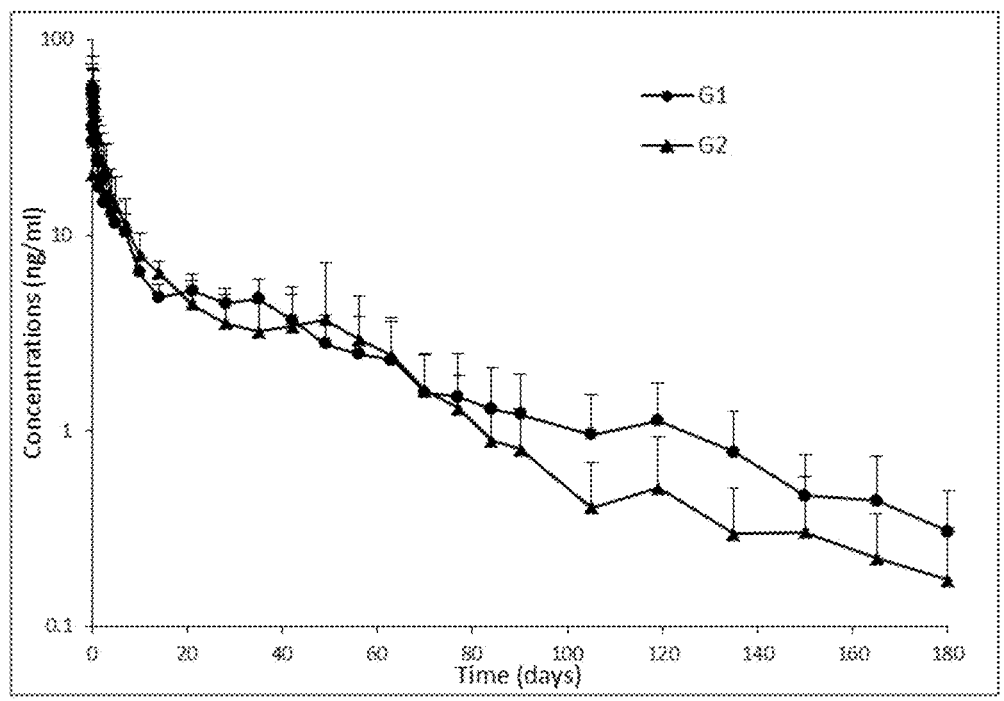
FIG. 5 depicts the pharmacokinetic profiles obtained following the administration of a 240 mg dose of lanreotide using: a composition (G1) comprising 47.50% (w/w) lanreotide, 19.00% (w/w) glycofurol, acetate, and water; or a composition (G2) comprising 40.00% (w/w) lanreotide, 16.50% (w/w) glycofurol, acetate, and water.
Figure 6:
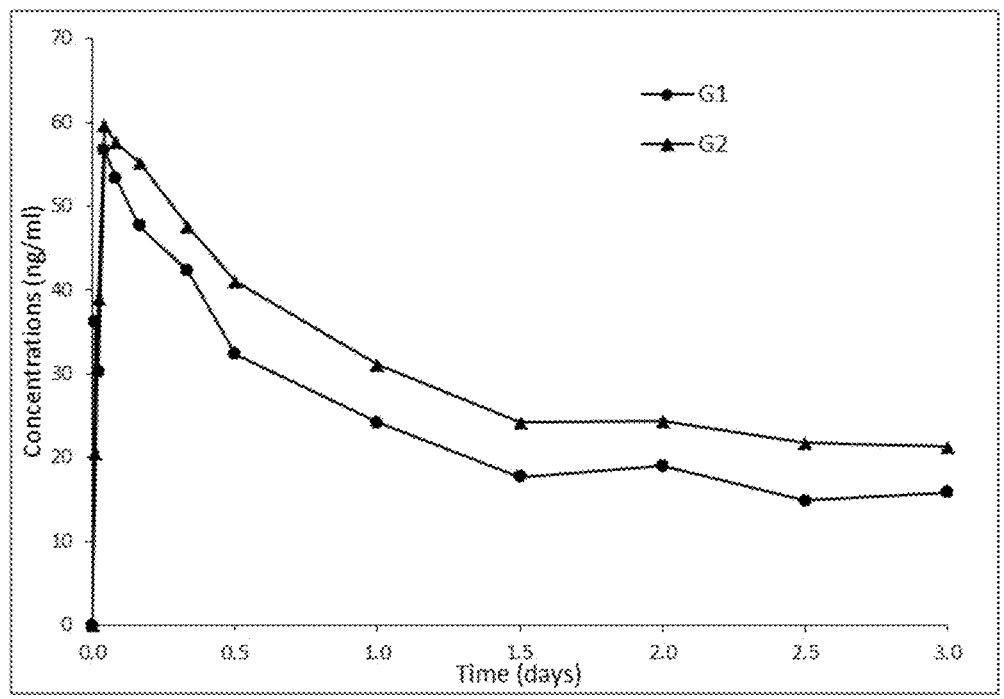
FIG. 6 depicts the pharmacokinetic profiles obtained following the administration of a 240 mg dose of lanreotide using: a composition (G1) comprising 47.50% (w/w) lanreotide, 19.00% (w/w) glycofurol, acetate, and water; or a composition (G2) comprising 40.00% (w/w) lanreotide, 16.50% (w/w) glycofurol, acetate, and water.

Resulting mean±SD pharmacokinetic profiles obtained in dogs for each formulation, i.e. G1 and G2, are presented in FIGS. 5 and 6. This PK study demonstrates the sustained release (SR) properties of these compositions.

Data have been normalized at 15 kg dog bodyweight. Dogs showing discharge during experiment or putative antibody in serum associated to lanreotide were removed for the analysis.

Example 2d

The pharmaceutical compositions identified in Examples 1i (F1), 1j (F2) and 1k (F3) are injected in dog at a dose of 240 mg of lanreotide. These compositions are reported in Table 3.

TABLE 3

| Composition | Content % (w/w) | | | |
|---|---|---|---|---|
| | Lanreotide | Acetate | PEG 600 | WFI |
| F1 | 40.00 | q.s. 8.11 | 20.51 | q.s. 100.00 |
| F2 | 36.00 | q.s. 7.75 | 20.10 | q.s. 100.00 |
| F3 | 36.00 | q.s. 8.00 | 18.00 | q.s. 100.00 |

A total of 12 Beagle dogs (6 males and 6 females) 7-13 kg bodyweight per formulation are used at the beginning of the study. They are maintained with free access to a dry standard diet and to drinkable water. The animals are subcutaneously administered in inter scapular area by trained personnel.

Blood samples are obtained from each dog through the jugular veins, before injection (time 0), 15 and 30 minutes, 1, 2, 4, 8 and 12 hours, 1, 1.5, 2, 2.5, 3 4, 5, 7, 10, 14, 21, 28, 35, 42, 49, 56, 63, 70, 77, 84, 90, 105, 120, 135, 150, 165 and 180 days after administration.

The blood samples remain at room temperature for a minimum of 30 min and then they are centrifuged (1600 g for 20 min at 4° C.) in the centrifuge.

The lanreotide serum concentration is determined by means of a validated RIA method that implies the preparation of calibrated standard curves and the inclusion of quality control samples. The limit of quantification is 80 pg·ml-1.

A non-compartmental pharmacokinetic analysis of the individual serum concentration-actual time profile is applied by means of the WinNonlin v5.2 software in order to obtain at least the following parameters: peak serum concentration (Cmax), time to peak (Tmax), area under the time-concentration curve from 0 to t (AUCt) and mean residence time from 0 to t (MRTt).

Figure 7:
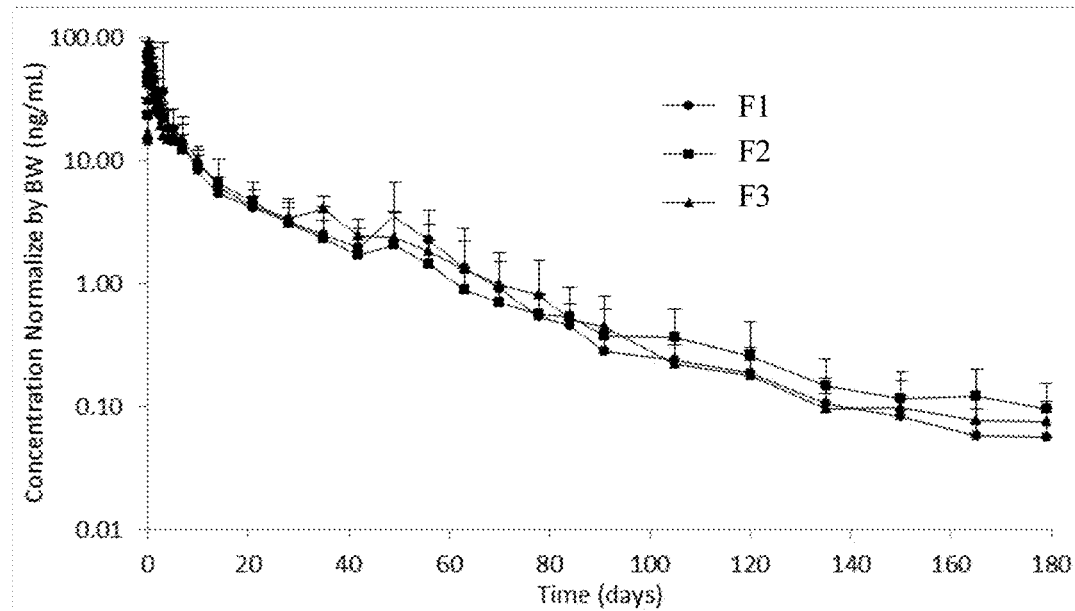
FIG. 7 depicts the pharmacokinetic profiles obtained following the administration of a 240 mg dose of lanreotide using: a composition (F1) comprising 40.00% (w/w) lanreotide, 20.51% (w/w) PEG 600, acetate, and water; a composition (F2) comprising 36.00% (w/w) lanreotide, 20.10% (w/w) PEG 600, acetate, and water; or a composition (F3) comprising 36.00% (w/w) lanreotide, 18.00% (w/w) PEG 600, acetate, and water.
Figure 8:
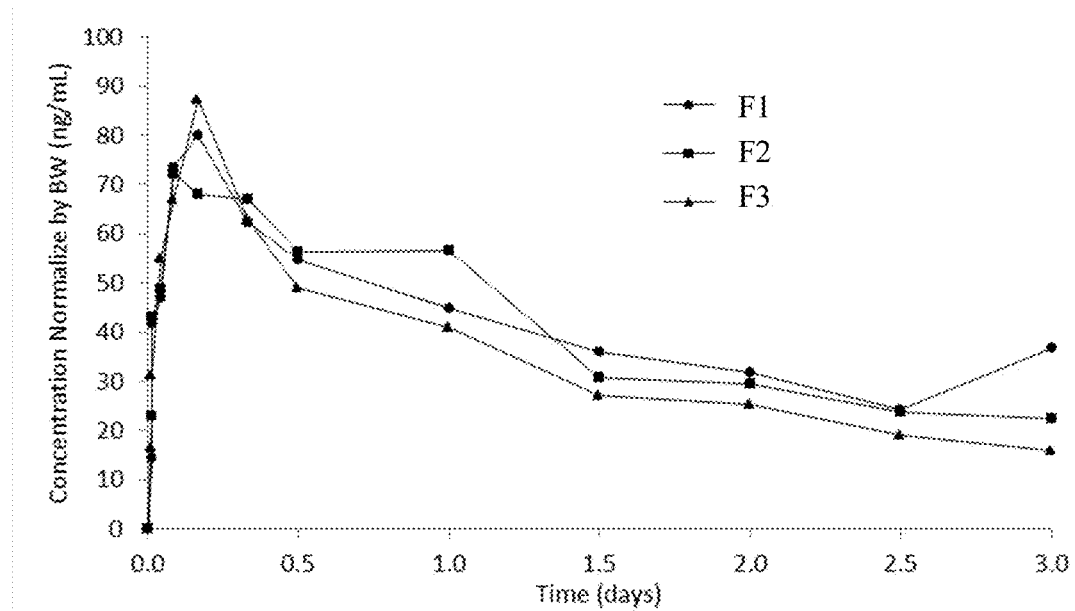
FIG. 8 depicts the pharmacokinetic profiles obtained following the administration of a 240 mg dose of lanreotide using: a composition (F1) comprising 40.00% (w/w) lanreotide, 20.51% (w/w) PEG 600, acetate, and water; a composition (F2) comprising 36.00% (w/w) lanreotide, 20.10% (w/w) PEG 600, acetate, and water; or a composition (F3) comprising 36.00% (w/w) lanreotide, 18.00% (w/w) PEG 600, acetate, and water.

Resulting mean±SD pharmacokinetic profiles obtained in dogs for each formulation, i.e. F1, F2 and F3, are presented in FIGS. 7 and 8. This PK study demonstrates the sustained release (SR) properties of these compositions.

Data have been normalized at 15 kg dog bodyweight. Dogs showing discharge during experiment or putative antibody in serum associated to lanreotide have been removed for the analysis.

Example 2e

The pharmaceutical composition identified in Example 1m (G3, batches B17 and B18) are injected in dog at a dose of 270 and 450 mg of lanreotide. This composition is reported in Table 4.

TABLE 4

| Composition | Content % (w/w) | | | |
|---|---|---|---|---|
| | Lanreotide | Acetate | Glycofurol | WFI |
| G3 | 44.00 | q.s. 8.00 | 18.50 | q.s. 100.00 |

A total of 16 Beagle dogs (eight males and eight females) 7-12 kg bodyweight per formulation are used at the beginning of the study. They are maintained with free access to a dry standard diet and to drinkable water. The animals are subcutaneously administered in inter scapular area by trained personnel.

Blood samples are obtained from unanesthetized animals by direct venipuncture from the jugular vein, before injection (time 0), 15 and 30 minutes, 1, 2, 4, 8 and 12 hours, 1, 1.5, 2, 2.5, 3, 4, 5, 7, 10, 14, 21, 28, 35, 42, 49, 56, 63, 70, 77, 84, 90, 105, 119 after administration.

The blood samples remain at room temperature for a minimum of 30 min and then they are centrifuged (1600 g for 20 min at 4° C.) in the centrifuge.

The lanreotide serum concentration is determined by means of a validated RIA method that implies the preparation of calibrated standard curves and the inclusion of quality control samples. The limit of quantification is 80 pg·ml$^{-1}$.

A non-compartmental pharmacokinetic analysis of the individual serum concentration-actual time profile is applied by means of the WinNonlin v5.2 software in order to obtain at least the following parameters: peak serum concentration ($C_{max}$), time to peak ($T_{max}$), area under the time-concentration curve from 0 to t (AUCt) and mean residence time from 0 to t (MRTt).

Figure 9:
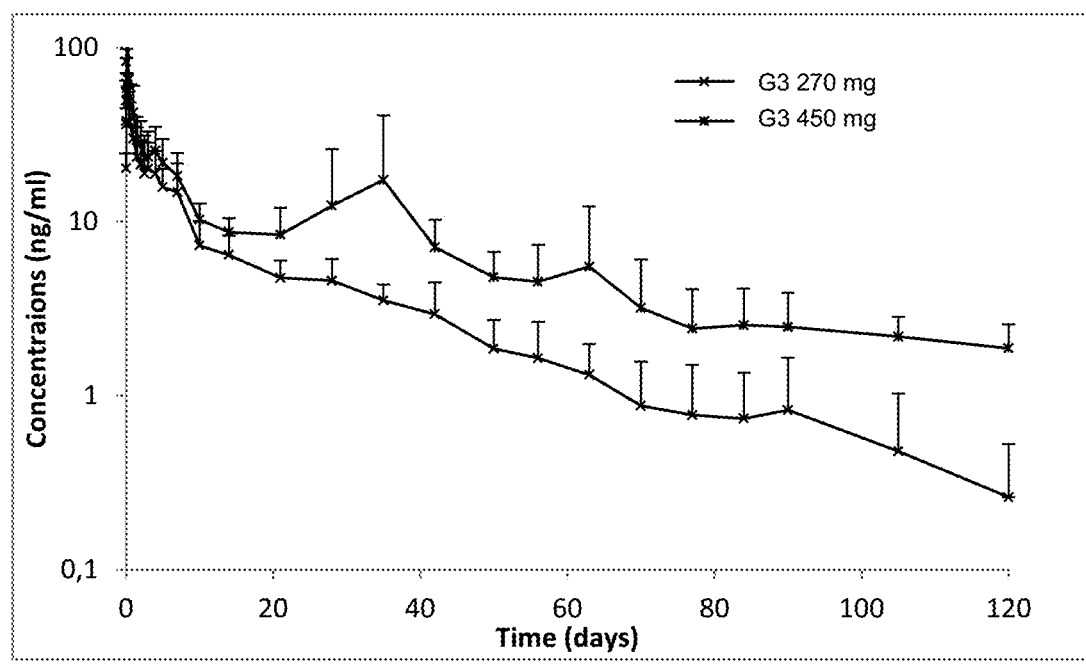
FIG. 9 depicts the pharmacokinetic profiles obtained following the administration of a 270 mg dose or a 450 mg dose of lanreotide using a composition comprising 44% (w/w) lanreotide, 18.5% (w/w) glycofurol, acetate, and water.

Resulting mean±SD pharmacokinetic profiles obtained in dogs for each lanreotide dose, i.e. 270 and 450 mg, are presented in FIG. 9 (lanreotide serum profiles determined in Beagle dogs following single SC Administration of G3 Formulation at the theoretical doses of 270 and 450 mg of pure peptide per dog). This PK study demonstrates the sustained release (SR) properties of these compositions.

Data have been normalized at 15 kg dog bodyweight. Dogs showing discharge during experiment or putative antibody in serum associated to lanreotide were removed for the analysis.

3—Stability Study

Example 3a

NMP Formulation

The pharmaceutical compositions of the present invention are stable when tested over time upon storage under the recommended 5° C. condition.

A stability study on the pharmaceutical compositions identified as B2 in Example 1a is launched at 5° C. and 25° C./60% RH (RH: relative humidity). The pharmaceutical composition is stored in pre-filled syringes.

The stability data are shown in Table 5 and Table 6.

TABLE 5 stability data at 5 ± 3° C.

| Batch | Parameter | T = 0 | T = 1 M | T = 3 M | T = 6 M | T = 9 M |
|---|---|---|---|---|---|---|
| B2 | Peptide content (%) | 47.1 | 46.7 | 46.2 | 48.3 | 46.3 |
| | Purity (RP-HPLC, % area) | 97.7 | 97.6 | 97.7 | 97.6 | 97.4 |
| | Oligomers (SEC, % area) | 0.9 | 1.7 | 1.9 | 1.8 | 1.7 |
| | Syringe Injection Force (SIF, N) | 20.7 | 20.5 | 21.9 | 21.4 | 20.2 |

TABLE 6 stability data at 25 ± 2° C./60 ± 5% RH

| Batch | Parameter | T = 0 | T = 1 M | T = 3 M |
|---|---|---|---|---|
| B2 | Peptide content (%) | 47.1 | 46.5 | 45.5 |
| | Purity (RP-HPLC, % area) | 97.7 | 96.8 | 96.2 |
| | Oligomers (SEC, % area) | 0.9 | 2.6 | 2.6 |
| | Syringe Injection Force (SIF, N) | 20.7 | 22.1 | 27.7 |

Example 3b

PEG Formulations

Stability results were generated on three different Lanreotide 3 months PEG formulations [F1 (at a dose of 60 mg of lanreotide), F2 (at a dose of 60 mg of lanreotide) and F3 (at a dose of 60 mg of lanreotide)] stored at the recommended 5° C. condition over a 9-month period. Some syringes were also stored in accelerated temperature conditions at 25° C./60% RH. Representative data at 5° C. is provided in Table 7.

Based on 9 months real time stability data, a provisional shelf-life of 18 months at 2-8° C. is proposed for the Lanreotide 3-month PEG formulations.

TABLE 7 stability data at 5° C.

| Composition | Parameter | T = 0 | T = 3 M | T = 6 M | T = 9 M |
|---|---|---|---|---|---|
| F2 (at a dose of 60 mg of lanreotide) | Appearance of syringe content | Off white | Off white | Off white | Slightly yellow |
| | Syringe Injection Force (SIF, N) Min/Max | 10.6/15.0 | 12.3/17.1 | 10.9/16.2 | 12.4/17.6 |
| | Peptide content (%) | 33.9 | 34.0 | 34.3 | 34.1 |
| | Injected Dose | 58.0 | 58.3 | 57.7 | 58.7 |

TABLE 7-continued stability data at 5° C.

| Composition | Parameter | T = 0 | T = 3 M | T = 6 M | T = 9 M |
|---|---|---|---|---|---|
| | (mg/syringe) | | | | |
| | Mass injectable (mg) | 171.4 | 171.4 | 168.2 | 172.3 |
| | RP-HPLC (%) | | | | |
| | Each Individual Impurities/ | 0.3 | 0.3 | 0.3 | 0.3 |
| | Total impurities ≥0.1% | 1.12 | 1.25 | 1.20 | 1.46 |
| | SE-HPLC Oligomers (%) | 1.74 | 1.87 | 1.89 | 2.00 |
| | pH | 4.7 | 4.7 | 4.7 | — |
| | Water Content (%) | 40.6 | — | — | — |

Example 3c

Glycofurol Formulations

Two different Lanreotide 3 months glycofurol formulations (G1: 47.5% of API and G2: 40% of API) were selected for an accelerated stability study based on Arrhenius methodology. This study was designed to determine the kinetic of degradation at different storage conditions over a small duration period.

The batches were stored for a 10 to 15-day period at 3 different storage conditions ranging from 40° C. to 55° C. The results are provided in Table 8.

TABLE 8

Arrhenius predictions based on sum of total impurities ≥0.1%

| Formulation | Degradation rate (k) at 5° C. (% impurity/year) |
|---|---|
| G1 | 0.04 |
| G2 | 0.01 |

Based on the data obtained during this Arrhenius study, similar degradation rates were observed at 5° C. for G1 and G2 formulations. In both cases, the shelf-life prediction based on the degradation rate observed supports a shelf-life prediction of approximately 24 months. This investigational study carried out in accelerated temperature conditions demonstrated the suitable stability of the proposed glycofurol based formulations.

The three different lanreotide glycofurol formulations (G1: 47.5% (w/w) of laneotide, G2: 40% (w/w) of lanreotide and G3:44% (w/w) of lanreotide) were selected for a stability study at 5° C. The results are provided in tables 9 to 11 below.

TABLE 9

Stability Data at 5° C. conditions (G1 formualtion)

| | Time point (months) | | | | |
|---|---|---|---|---|---|
| Test | 0 | 3 | 6 | 9 | 12 |
| Mean concentration of lanreotide (% w/w) | 44.0 | 42.5 | 42.3 | 43.4 | 42.8 |
| Total impurities ≥0.1% (% area) | 4.2 | 5.9 | 7.3 | 6.3 | 7.8 |
| pH | 5.0 | 5.1 | 5.0 | 5.1 | 5.0 |
| Maximum SIF (N) | 27 | 29 | 24 | 28 | 27 |

TABLE 10

Stability Data at 5° C. conditions (G2 formualtion)

| | Time point (months) | | | | |
|---|---|---|---|---|---|
| Test | 0 | 3 | 6 | 9 | 12 |
| Mean concentration of lanreotide (% w/w) | 38.5 | 38.1 | 37.8 | 38.7 | 38.2 |
| Total impurities ≥0.1% (% area) | 2.5 | 2.6 | 2.9 | 2.6 | 3.0 |
| pH | 4.9 | 4.9 | 4.9 | 4.9 | 4.9 |
| Maximum SIF (N) | 28 | 34 | 35 | 31 | 34 |

TABLE 11

Stability Data at 5° C. conditions (G3 formualtion)

| | Time point (months) | | | |
|---|---|---|---|---|
| Test | 0 | 3 | 6 | 9 |
| Mean concentration of lanreotide (% w/w) | 43.1 | 43.2 | 42.9 | 43.2 |
| Total impurities ≥0.1% (% area) | 1.7 | 1.4 | 1.4 | 1.6 |
| pH | 4.9 | 4.9 | 4.9 | 5.0 |
| Maximum SIF (N) | 25 | 21 | 27 | 24 |

Lanreotide mean concentration is performed by HPLC with a reverse phase method using a C18 stationary phase with gradient elution. Quantitative analysis is carried out using an external standard by comparing peak area (Column: Symetry C18 100 mm×4.6 mm; 3.5 μm or equivalent; Flow rate: 1 mL/min; UV detection at 280 nm; Mobile phase: mixture of acetonitrile/water/trifluoroacetic acid; Reference standard and sample diluent: 0.1 M acetic acid).

Impurities are tested using the same method as for mean concentration determination. The amount of an impurity present in a sample is calculated from the peak area of the impurity relative to the peak area of lanreotide. A relative response factor of 1 is used. Total impurities are expressed as the sum of the impurity values above 0.1%.

The invention claimed is:

1. A pharmaceutical composition consisting of:
   lanreotide, present at a concentration of from 42% to 46% of the total weight of the composition;
   one or more glycofurols of formula (I),

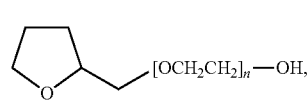

(I)

wherein n is an integer from 1 to 5; and
   wherein the one or more glycofurols is present at a concentration of from 16% to 20% of the total weight of the composition;

acetic acid;

an additive selected from a stabilizer, an antioxidant, and/or a surfactant, wherein the additives is present in an amount of from 0 to 5% of the total weight of the composition; and water (q.s. 100%);

wherein the pH of the composition is from 4.0 to 6.0.

2. The composition of claim 1, wherein the pH of the composition is from 4.8 to 5.4.

3. The composition of claim 1, wherein the total amount of additive in the composition is less than 1% of the total weight of the composition.

4. A method of treating acromegaly or a neuroendocrine tumor, the method comprising administering a therapeutically-effective amount of the composition of claim 1 to a patient in need thereof.

5. The method according to claim 4 wherein the composition is administered parenterally.

6. The composition of claim 1, wherein lanreotide is in salt form.

7. The composition of claim 1, wherein lanreotide is in the form of lanreotide acetate.

\* \* \* \* \*